US010709606B2

(12) United States Patent
Zickler et al.

(10) Patent No.: US 10,709,606 B2
(45) Date of Patent: Jul. 14, 2020

(54) METHODS OF LASER MODIFICATION OF INTRAOCULAR LENS

(71) Applicant: AMO Development, LLC, Santa Ana, CA (US)

(72) Inventors: Leander Zickler, Bend, OR (US); Jim Deacon, Goleta, CA (US)

(73) Assignee: AMO Development, LLC, Santa Ana, CA (US)

( * ) Notice: Subject to any disclaimer, the term of this patent is extended or adjusted under 35 U.S.C. 154(b) by 299 days.

(21) Appl. No.: 15/688,533

(22) Filed: Aug. 28, 2017

(65) Prior Publication Data
US 2018/0008462 A1 Jan. 11, 2018

Related U.S. Application Data

(62) Division of application No. 14/531,716, filed on Nov. 3, 2014, now Pat. No. 9,744,077, which is a division
(Continued)

(51) Int. Cl.
*A61F 9/008* (2006.01)
*A61F 2/16* (2006.01)
(Continued)

(52) U.S. Cl.
CPC ............... *A61F 9/008* (2013.01); *A61F 2/16* (2013.01); *A61F 2/1624* (2013.01);
(Continued)

(58) Field of Classification Search
CPC ......... A61F 2/16; A61F 2/1624; A61F 2/1629
See application file for complete search history.

(56) References Cited

U.S. PATENT DOCUMENTS

| 4,134,161 A | 1/1979 | Bayers |
| 4,136,466 A | 1/1979 | Wrue |

(Continued)

FOREIGN PATENT DOCUMENTS

| CA | 2664105 C | 12/2014 |
| DE | 102006036800 A1 | 2/2008 |

(Continued)

OTHER PUBLICATIONS

Ayaki M., et al., "Histopathologic Study of After-Cataract in the Pseudophakic Rabbit Eye Using in-the-Bag Fixation (II)," Nippon Ganka Gakkai Zasshi, 1990, vol. 94 (6), pp. 559-565—Abstract Only.

(Continued)

*Primary Examiner* — Christopher A Flory
(74) *Attorney, Agent, or Firm* — Johnson & Johnson Surgical Vision, Inc.

(57) ABSTRACT

A method of modifying a refractive profile of an eye having an intraocular device implanted therein, wherein the method includes determining a corrected refractive profile for the eye based on an initial refractive profile, identifying one or more locations within the intraocular device based on the corrected refractive profile, and directing a pulsed laser beam at the locations to produce the corrected refractive profile. A system of modifying an intraocular device located within an eye, wherein the system includes a laser assembly and a controller coupled thereto. The laser assembly outputs a pulsed laser beam having a pulse width between 300 picoseconds and 10 femtoseconds. The controller directs the laser assembly to output the pulsed laser beam into the intraocular device. One or more slip zones are formed within the intraocular device in response thereto, and the slip zones are configured to modify a refractive profile of the intraocular device.

3 Claims, 9 Drawing Sheets

Related U.S. Application Data of application No. 12/239,462, filed on Sep. 26, 2008, now abandoned.

(51) Int. Cl.
*A61F 9/007* (2006.01)
*A61F 9/00* (2006.01)

(52) U.S. Cl.
CPC ........ *A61F 2/1629* (2013.01); *A61F 9/00834* (2013.01); *A61F 9/007* (2013.01); *A61F 9/0017* (2013.01); *A61F 2002/1681* (2013.01); *A61F 2002/1699* (2015.04); *A61F 2009/0087* (2013.01); *A61F 2009/0088* (2013.01); *A61F 2009/00848* (2013.01); *A61F 2250/0006* (2013.01); *A61F 2250/0008* (2013.01); *G02C 2202/14* (2013.01)

(56) References Cited

U.S. PATENT DOCUMENTS

| | | | |
|---|---|---|---|
| 4,219,721 A | 8/1980 | Kamen et al. | |
| 4,403,354 A | 9/1983 | Rainin | |
| 4,435,855 A | 3/1984 | Pannu | |
| 4,443,441 A | 4/1984 | Galin | |
| 4,463,457 A | 8/1984 | Kelman | |
| 4,559,942 A | 12/1985 | Eisenberg | |
| 4,575,373 A | 3/1986 | Johnson | |
| 4,585,456 A | 4/1986 | Blackmore | |
| 4,617,023 A | 10/1986 | Peyman | |
| 4,642,113 A | 2/1987 | Dubroff | |
| 4,661,109 A | 4/1987 | White | |
| 4,662,882 A | 5/1987 | Hoffer | |
| 4,666,445 A | 5/1987 | Tillay | |
| 4,676,793 A | 6/1987 | Bechert, II | |
| 4,681,585 A | 7/1987 | Sayano et al. | |
| 4,685,921 A | 8/1987 | Peyman | |
| 4,685,922 A | 8/1987 | Peyman | |
| 4,687,485 A | 8/1987 | Lim et al. | |
| 4,704,016 A | 11/1987 | De Carle | |
| 4,764,930 A | 8/1988 | Bille et al. | |
| 4,781,718 A | 11/1988 | Lindstrom | |
| 4,834,753 A | 5/1989 | Sulc et al. | |
| 4,872,876 A | 10/1989 | Smith | |
| 4,946,470 A | 8/1990 | Sulc et al. | |
| 5,108,429 A | 4/1992 | Wiley | |
| 5,147,395 A | 9/1992 | Willis | |
| 5,217,491 A | 6/1993 | Vanderbilt | |
| 5,225,858 A | 7/1993 | Portney | |
| 5,259,813 A | 11/1993 | Abthoff et al. | |
| 5,269,813 A | 12/1993 | Yoshida et al. | |
| 5,288,293 A | 2/1994 | O'Donnell | |
| 5,571,177 A | 11/1996 | Deacon et al. | |
| 5,713,892 A | 2/1998 | Shimmick | |
| 5,728,156 A | 3/1998 | Gupta et al. | |
| 5,984,962 A | 11/1999 | Anello et al. | |
| 5,993,438 A | 11/1999 | Juhasz et al. | |
| 6,210,005 B1 | 4/2001 | Portney | |
| 6,887,083 B2 | 5/2005 | Umeyama et al. | |
| 6,923,955 B2 | 8/2005 | Till et al. | |
| 7,044,945 B2 | 5/2006 | Sand | |
| 2001/0010019 A1 | 7/2001 | Schachar | |
| 2002/0103478 A1 | 8/2002 | Gwon et al. | |
| 2002/0173846 A1* | 11/2002 | Blake | A61F 2/1613 623/6.18 |
| 2003/0028248 A1 | 2/2003 | Shahinpoor et al. | |
| 2004/0049174 A1* | 3/2004 | Peyman | A61F 2/147 606/5 |
| 2004/0082993 A1 | 4/2004 | Woods | |
| 2004/0111153 A1 | 6/2004 | Woods et al. | |
| 2004/0153150 A1 | 8/2004 | Ghazizadeh et al. | |
| 2004/0184158 A1* | 9/2004 | Shadduck | A61F 2/1613 359/665 |
| 2004/0199149 A1 | 10/2004 | Myers et al. | |
| 2004/0243111 A1 | 12/2004 | Bendett et al. | |
| 2005/0246019 A1* | 11/2005 | Blake | A61F 2/1613 623/6.46 |
| 2006/0061729 A1* | 3/2006 | Shadduck | A61F 2/1613 351/159.01 |
| 2006/0253196 A1 | 11/2006 | Woods | |
| 2006/0265058 A1 | 11/2006 | Silvestrini | |
| 2007/0185475 A1 | 8/2007 | Frey et al. | |
| 2007/0299487 A1* | 12/2007 | Shadduck | A61F 2/1613 607/89 |
| 2008/0140192 A1 | 6/2008 | Humayun et al. | |
| 2008/0161913 A1 | 7/2008 | Brady et al. | |
| 2008/0161914 A1 | 7/2008 | Brady et al. | |
| 2010/0292678 A1 | 11/2010 | Frey et al. | |

FOREIGN PATENT DOCUMENTS

| | | |
|---|---|---|
| EP | 94158 A1 | 11/1983 |
| EP | 0278724 A2 | 8/1988 |
| EP | 336318 A2 | 10/1989 |
| EP | 478929 A1 | 4/1992 |
| SU | 1424828 A1 | 9/1988 |
| WO | 8701931 A1 | 4/1987 |
| WO | 9007914 A1 | 7/1990 |
| WO | 0182815 A1 | 11/2001 |
| WO | 02071976 A2 | 9/2002 |
| WO | 03057081 A2 | 7/2003 |
| WO | 2004039295 A1 | 5/2004 |
| WO | 2004039395 A1 | 5/2004 |
| WO | 04082542 A2 | 9/2004 |
| WO | 2007084602 A2 | 7/2007 |
| WO | 2010059847 A1 | 5/2010 |

OTHER PUBLICATIONS

Ayaki M., et al., "Histopathologic Study of After-Cataract in the Pseudophakic Rabbit Eye Using Out-of-the-Bag Fixation," Nippon Ganka Gakkai Zasshi, 1990, vol. 94 (6), pp. 553-558—Abstract Only.

Biedner B., et al., "Subconjunctival Dislocation of Intraocular Lens Implant," American Journal of Opthalmology, 1977, vol. 84 (2), pp. 265-266.

Bloom S.M., et al., "Scleral Fixation Suture for Dislocated Posterior Chamber Intraocular Lens," Ophthalmic Surgery, 1990, vol. 21 (12), pp. 851-854.

Bowman C.B., et al., "Noninvasive Repositioning of a Posterior Chamber Intraocular Lens Following Pupillary Capture," Journal of Cataract and Refractive Surgery, 1991, vol. 17 (6), pp. 843-847.

Chan B.P., et al., "Effects of Photochemical Crosslinking on the Microstructure of Collagen and a Feasibility Study on Controlled Protein Release," Acta Biomaterialia, 2008, vol. 4 (6), pp. 1627-1636.

Chan C.K., "An Improved Technique for Management of Dislocated Posterior Chamber Implants," Ophthalmology, 1992, vol. 99 (1), pp. 51-57.

Corcoran M.F., "Spontaneous Repositioning of a Dislocated Medallion Intraocular Lens," Journal of the American Intra-Ocular Implant Society, 1985, vol. 11 (6), pp. 598-599.

European Search Report for Application No. EP16181235, dated Jan. 5, 2017, 8 pages.

Flynn H.W., et al., "Management of Subluxated and Posteriorly Dislocated Intraocular Lenses Using Pars Plana Vitrectomy Instrumentation," Journal of Cataract and Refractive Surgery, 1990, vol. 16 (1), pp. 51-56.

Flynn H.W., "Pars Plana Vitrectomy in the Management of Subluxed and Posteriorly Dislocated Intraocular Lenses," Graefe's Archive for Clinical and Experimental Ophthalmology, 1987, vol. 225 (3), pp. 169-172.

Friedberg M.A., et al., "A New Technique for Repositioning and Fixating a Dislocated Intraocular Lens," Archives of Ophthalmology, 1992, vol. 110 (3), pp. 413-415.

Glasser A., "Accommodation" in: Encyclopedia of Eye, vol. 1, Dartt D.A., ed., Oxford Academic Press, 2010, pp. 8-17.

Glasser A., et al., "Accommodation and Presbyopia" in: Adler's Physiology of the Eye, Clinical Application, 10th Edition and 7th Chapter, Kaufman P.L., et al., Eds., Mosby, 2002, pp. 195-233.

(56) References Cited

OTHER PUBLICATIONS

Glasser A., "Physiology of Accommodation and Presbyopia" in: Surgery for Hyperopia, Chapter. 2, Sher N.A., Ed., SLACK, Inc., 2004, pp. 11-21.

Glasser A., "The Helmholtz Mechanism of Accommodation" in: Hyperopia and Presbyopia, Chapter 3, Tsubota K., et al., eds., Marcel Dekker, Inc., 2003, pp. 27-47.

Henderson B.A., et al., "Stepwise Approach to Establishing an Ophthalmology Wet Laboratory," Journal of Cataract & Refractive Surgery, 2009, vol. 35 (6), pp. 1121-1128.

Hovanesian J.A., et al., "Cataract Wound Closure with a Polymerizing Liquid Hydrogel Ocular Bandage," Journal of Cataract & Refractive Surgery, 2009, vol. 35 (5), pp. 912-917.

Hovanesian J.A., et al., "Watertight Cataract Incision Closure Using Fibrin Tissue Adhesive," Journal of Cataract & Refractive Surgery, 2007, vol. 33 (8), pp. 1461-1463.

International Preliminary Report on Patentability and Written Opinion for Application No. PCT/US2010/050752, dated Apr. 3, 2012, 9 pages.

International Search Report and Written Opinion for Application No. PCT/US2012/028090, dated Sep. 25, 2012, 19 Pages.

International Search Report and Written Opinion for Application No. PCT/US2012/028095, dated Jun. 19, 2012, 11 pages.

International Search Report and Written Opinion, dated Jan. 14, 2010, and International Preliminary Report on Patentability, dated Mar. 29, 2011, for Application No. PCT/US2009/058321, 11 pages.

International Search Report for Application No. PCT/US2010/050752, dated Mar. 22, 2011, 5 pages.

International Search Report for Application No. PCT/US94/06403, dated Sep. 20, 1994, 4 pages.

Lyons C.J., et al., "Report of a Repositioned Posteriorly Dislocated Intraocular Lens via Pars Plicata Sclerotomy," Journal of Cataract Refractive Surgery, 1990, vol. 16 (4), pp. 509-511.

Menabeuoni L., et al., "Laser-Assisted Corneal Welding in Cataract Surgery: Retrospective Study," Journal of Cataract and Refractive Surgery, 2007, vol. 33 (9), pp. 1608-1612.

Moretsky S.L., "Suture Fixation Technique for Subluxated Posterior Chamber IOL through Stab Wound Incision," Journal of the American Intra-Ocular Implant Society, 1984, vol. 10 (4), pp. 477-480.

Nabors G., et al., "Ciliary Sulcus Suturing of a Posterior Chamber Intraocular Lens," Ophthalmic Surgery, 1990, vol. 21 (4), pp. 263-265.

Neumann A.C., et al., "Complications Associated with STAAR Silicone Implants," Journal of Cataract and Refractive Surgery, 1987, vol. 13 (6), pp. 653-656.

Nevyas H.J., et al., "A YAG Laser Technique to Facilitate Removal of Posterior Chamber Intraocular Lenses from the Capsular Bag," Journal of Cataract and Refractive Surgery, 1987, vol. 13 (2), pp. 201-204.

Pandey S.K., et al., "Creating Cataracts of Varying Hardness to Practice Extracapsular Cataract Extraction and Phacoemulsification," Journal of Cataract & Refractive Surgery, 2000, vol. 26 (3), pp. 322-329.

Pandey S.K., et al., "Induction of Cataracts of Varying Degrees of Hardness in Human Eyes Obtained Postmortem for Cataract Surgeon Training," American Journal of Ophthalmology, 2000, vol. 129 (4), pp. 557-558.

Partial International Search Report for Application No. PCT/US2012/028090, dated May 29, 2012, 6 pages.

Pau H., "Cortical and Subcapsular Cataracts: Significance of Physical Forces," Ophthalmologica, 2006, vol. 220 (1), pp. 1-5.

Poley B.J., et al., "A Closed Technique for Repositioning Dislocated Iris Plane Lenses," Journal of the American Intra-Ocular Implant Society, 1979, vol. 5 (4), pp. 316-320.

Praeger D.L., "Praeger Micro Irrigating Hook Intraocular Lens Implantation," Ophthalmic Surgery, 1979, vol. 10 (7), pp. 30-32.

Ripken T., et al., "Fs-Laser Induced Elasticity Changes to Improve Presbyopic Lens Accommodation," Graefe's Archive for Clinical and Experimental Ophthalmology, 2008, vol. 246 (6), pp. 897-906.

Shentu X., et al., "Combined Microwave Energy and Fixative Agent for Cataract Induction in Pig Eyes," Journal of Cataract & Refractive Surgery, 2009, vol. 35 (7), pp. 1150-1155.

Smiddy W.E., "Dislocated Posterior Chamber Intraocular Lens: A New Technique of Management," Archives of Ophthalmology, 1989, vol. 107 (11), pp. 1678-1680.

Smiddy W.E., et al., "Management of Dislocated Posterior Chamber Intraocular Lenses," Ophthalmology, 1991, vol. 98 (6), pp. 889-894.

Stark W.J., et al., "Management of Posteriorally Dislocated Intraocular Lenses," Ophthalmic Surgery, 1980, vol. 11 (8), pp. 495-497.

Sternberg P., et al., "Treatment of Dislocated Posterior Chamber Intraocular Lenses," Archives of Ophthalmology, 1986, vol. 104 (9), pp. 1391-1393.

Sugiura T., et al., "Creating Cataract in a Pig Eye," Journal of Cataract & Refractive Surgery, 1999, vol. 25 (5), pp. 615-621.

Tseng Y., et al., "How Actin Crosslinking and Bundling Proteins Cooperate to Generate an Enhanced Cell Mechanical Response," Biochemical and Biophysical Research Communications, 2005, vol. 334 (1), pp. 183-192.

Wand M., et al., "Thymoxamine Hydrochloride:An Alpha-adrenergic Blocker," Survey of Ophthalmology, 1980, vol. 25 (2), pp. 75-84.

Weeber H.A., et al., "The Role of the Capsular Bag in Accommodation" in: Current Aspects of Human Accommodation II, Guthoff R., eds., Heidelberg, Kaden Verlag, 2003, pp. 119-126.

\* cited by examiner

METHODS OF LASER MODIFICATION OF INTRAOCULAR LENS

RELATED APPLICATIONS

The present application is a divisional of and claims priority to U.S. patent application Ser. No. 14/531,716, filed Nov. 3, 2014, which is a divisional of U.S. patent application Ser. No. 12/239,462, filed Sep. 26, 2008, the entire content of which are incorporated herein by reference.

The present application is a divisional of U.S. patent application Ser. No. 12/239,462, filed Sep. 26, 2008, the entire content of which is incorporated herein by reference.

FIELD OF THE INVENTION

The present invention relates generally to intraocular lenses and more particularly, to systems and methods for modifying in-situ intraocular lenses.

BACKGROUND

When the natural lens of the eye becomes cataractous, the natural lens may be replaced with an intraocular lens. The natural lens may also be replaced with an intraocular lens to correct other visual conditions, for example, to provide accommodation or pseudo-accommodation when presbyopia develops, which limits the focus capability of the eye on both distant objects and near objects. Accommodating and/or multifocal intraocular lenses may be used to restore at least some degree of accommodative or pseudo-accommodative ability. In general, accommodating intraocular lenses are configured to provide focus on objects over a range of distances (e.g., by axial displacement and/or by shape change in response to ocular forces, such as those produced by the ciliary muscle, zonules, and/or the capsular bag of the eye).

At times, the position of the intraocular lens within the eye may change after the insertion procedure has been completed. Additionally, inaccurate, pre-operative eye measurements (e.g., used to select the intraocular lens properties or position the same within the eye) may require changes to the position or effective refractive properties of the intraocular lens. U.S. Pat. No. 5,571,177 describes an intraocular lens having a fixation member with an alterable portion structured to be altered after the intraocular lens is placed in the eye. For example, a Nd:YAG laser is described in U.S. Pat. No. 5,571,177 for producing a laser beam to break the alterable portion of the fixation member. The Nd:YAG crystal associated with this laser can typically generate a laser beam with a pulse width no shorter than about 10 picoseconds, which limits the type, degree, and precision of structure alteration.

It is desirable to provide improved methods and systems of modifying the position of in-situ intraocular devices (e.g., intraocular lenses positioned within the eye). It is also desirable to provide methods and systems for modifying the refractive profile of the eye via modification of in-situ intraocular devices. The term "refractive profile" is used herein to generally describe the optical properties associated with an eye, which may be determined by a variety of techniques including, by way of example and not limitation, wavefront determination In particular, it is desirable to provide an ophthalmic surgical system and a method of ophthalmic surgery for re-positioning an in-situ intraocular lens via precision alteration of one or more support elements. It is also desirable to provide an ophthalmic surgical system and a method of ophthalmic surgery for assembling separately implanted components of an in-situ intraocular device. Additionally, other desirable features and characteristics of the present invention will become apparent from the subsequent detailed description and the appended claims, taken in conjunction with the accompanying drawings and the foregoing technical field and background.

SUMMARY OF THE INVENTION

The present invention is generally directed to ophthalmic devices, systems, and methods for modification of an in-situ intraocular device (e.g., an intraocular lens) using a laser system that may be directed through ocular anatomy to photoalter the intraocular device at a desired focal point. Laser energy may be directed into one or more portions of the intraocular device (e.g., at a support element or an optic of the intraocular lens) to modify the intraocular device. One advantage is that the intraocular lens may be altered, positionally adjusted to fine-tune a desired refractive correction, or the like, after the intraocular lens has been inserted or implanted. Refractive properties associated with the cornea may also be taken into account when altering the intraocular lens or while positionally adjusting the intraocular lens. For example, real-time refractive analysis (e.g., provided by a wavefront aberrometer, a topographer, or the like) of one or more components of the eye may be concurrently used during positioning to correlate the position of the intraocular lens with the desired refractive correction.

In one embodiment, a system for modifying an intraocular device located within an eye is provided. The system includes a laser assembly and a controller coupled to the laser assembly. The laser assembly is configured to output a pulsed laser beam having a pulse width between about 300 picoseconds and about 10 femtoseconds. The controller is configured to direct the laser assembly to output the pulsed laser beam into the intraocular device. The pulsed laser beam forms one or more slip zones within the intraocular device, and the slip zone(s) are configured to alter a refractive property associated with the intraocular device.

In another embodiment, a method of modifying a refractive profile associated with an eye having an intraocular device implanted therein is provided. The method includes determining a corrected refractive profile based on an initial refractive profile of the eye, identifying one or more locations within the intraocular device based on the corrected refractive profile, directing a pulsed laser beam at the one or more locations to produce the corrected refractive profile.

In another embodiment, a system is provided for modifying an intraocular device having a surface region and one or more subsurface regions. The system includes a laser assembly configured to output a pulsed laser beam and a processing unit coupled to the laser assembly. The processing unit is configured to control the laser assembly to direct the pulsed laser beam at one or more subsurface regions of the intraocular device. The one or more subsurface regions being structurally altered in response to the pulsed laser beam while maintaining a mechanical property of the surface region.

In another embodiment, a method is provided for modifying a refractive profile associated with an eye via an intraocular device. The method includes implanting an optic of the intraocular device within the eye, implanting a support element of the intraocular device within the eye, and directing a pulsed laser beam into both of the support element and the optic to fuse the support element to the optic. The intraocular device within the eye configured to modify the refractive profile.

BRIEF DESCRIPTION OF THE DRAWINGS

In the drawings, wherein like reference numerals refer to similar components.

DETAILED DESCRIPTION

Figure 1:
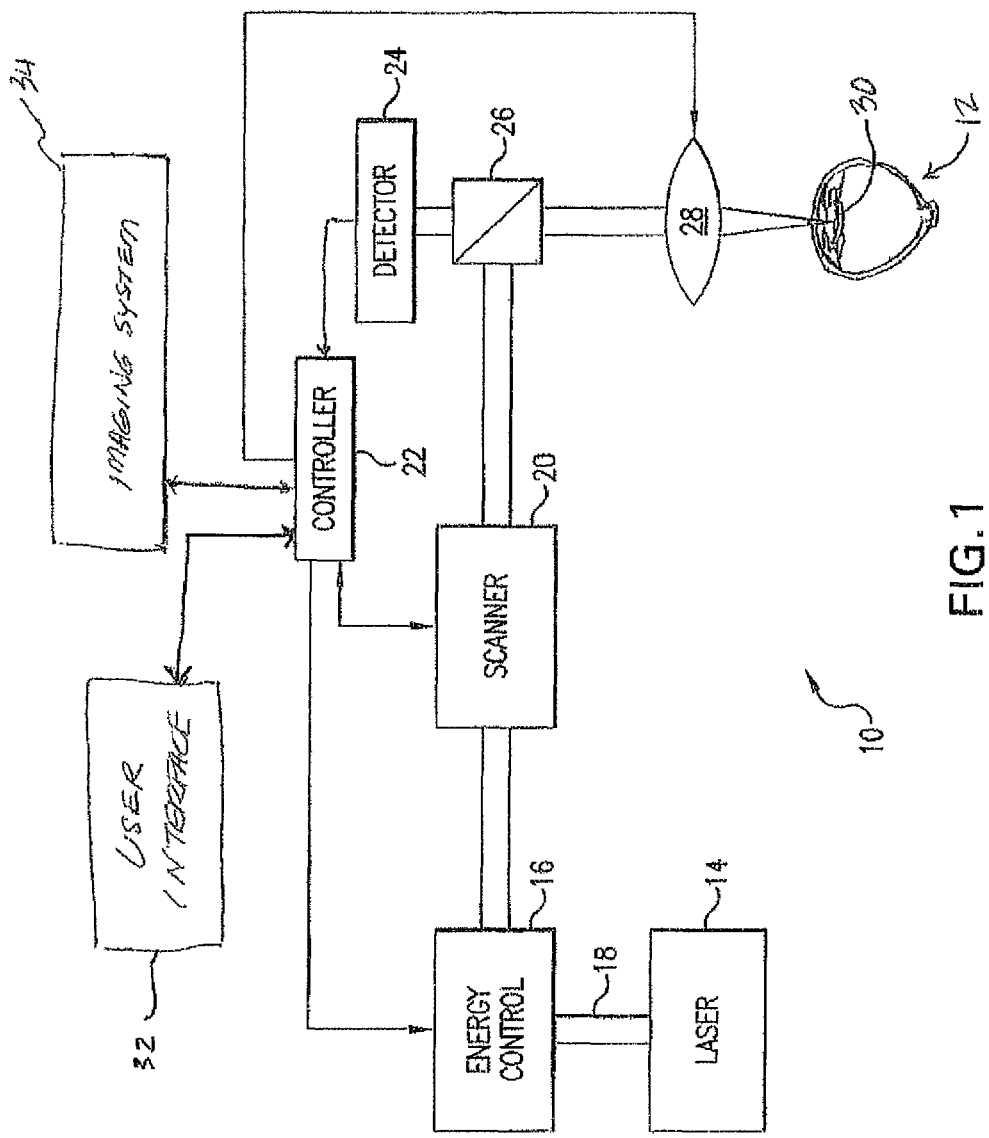
FIG. 1 is a block diagram of a system for modifying an in-situ intraocular device in accordance with one embodiment of the present invention.

The present invention generally provides systems and methods for modifying an intraocular lens, particularly an in-situ (e.g., positioned within an eye) intraocular lens, although these systems and methods can also modify intraocular lenses prior to implant or insertion. The systems and methods are utilized to structurally modify one or more subsurface regions within the intraocular lens while maintaining the mechanical or structural nature (i.e., prior to this modification) of the surface region of the intraocular lens. In one embodiment, subsurface regions of one or more support elements (e.g., a haptic or other support element coupled to the optic of the intraocular lens) of the in-situ intraocular lens are modified to adjust the position of the intraocular lens within the eye. Laser energy (e.g., supplied by a laser system outputting a pulsed laser beam having a pulse width within a femtosecond range) is used to irradiate the desired subsurface regions of the in situ intraocular lens. In another embodiment, laser energy may also be used to irradiate subsurface regions within the optic to alter the mechanical properties of the optic (e.g., to increase viscoelasticity, create a plastic effect, or the like).

With these systems and methods, the mechanical or structural properties of the optic and/or haptic (or other support element) associated with the in situ intraocular lens may also be advantageously modified in a non-intrusive or minimally intrusive manner. In one embodiment, the pulsed laser beam forms one or more slip zones in the intraocular lens. The term "slip zone" is defined herein to be a region of material (e.g., in the optic or support element) configured to have one portion capable of translational displacement with respect to an adjacent portion, such as in response to certain movements of the capsular bag containing the intraocular lens after implantation/insertion. As a result, the position of the intraocular lens within the eye may be finely adjusted in one or more directions (e.g., anteriorly, posteriorly, rotationally, vertically, horizontally, tilted, combinations of one or more of the foregoing, and the like). For example, the intraocular lens may be re-oriented such that the anterior surface of the optic abuts the anterior portion of the capsular bag. A variety of re-orientations of an in situ intraocular lens are thus possible. Additionally, the formation of one or more slip zones in the optic can be used to facilitate some degree of accommodation capability of the intraocular lens or enhance accommodation capability that has been pre-engineered in the intraocular lens.

The systems and methods of the present invention are well suited for customizing (e.g., fitting or adjusting) intraocular lenses to a particular recipient. For example, as a result of modifying one or more subsurface regions of the intraocular lens (e.g., a haptic), the intraocular lens may be horizontally displaced, vertically displaced, displaced towards the cornea, displaced towards the retina, rotated, tilted, and the like, or any combination thereof.

While used to modify in-situ intraocular lenses, the systems and methods of the present invention may also be used to modify intraocular lenses prior to implantation (e.g., modify a haptic or structure coupling the haptic to the optic or join and fix the haptic to the optic), such as during manufacture of the intraocular lens, customization of the intraocular lens biomechanics to implement a refractive correction for a particular recipient, pre-implantation/insertion assembly, and the like. Additionally, other intraocular devices replacing the natural lens in the eye can be modified by these systems and methods.

In one embodiment, a laser assembly outputting a non-ultraviolet (UV), ultrashort pulsed laser beam (e.g., having a pulse duration or pulse width as long as a few picoseconds or as short as a few femtoseconds) is used to provide the laser energy for subsurface modifications of the in-situ intraocular lens. This pulsed laser beam has a wavelength permitting passage of the pulsed laser beam through the cornea and other tissue or fluids between the intraocular lens and the outer surface of the cornea while minimizing or preventing energy absorption by such tissue or fluids except at the focal point of the pulsed laser beam. The laser assembly can be used to perform post-implant procedure adjustments to the intraocular lens or assembly thereof following a recovery period (e.g., for the eye to recover from the procedure). During this recovery period, the intraocular lens may settle to a more permanent position within the eye. The laser assembly may also be used during the implant procedure to modify the support element(s) of the intraocular lens from a state that is more favorable for insertion through an inserter to a state that is better suited for operation of the intraocular lens within the eye. By modifying a subsurface region of the intraocular lens, the intraocular lens is re-oriented or modified while minimizing potential leaching or particulate production.

Referring to the drawings, a system 10 for modifying an in-situ intraocular lens 30 is shown in FIG. 1 in accordance with one embodiment. The system 10 is suitable for ophthalmic applications and may be used to photoalter a variety of materials (e.g., organic, inorganic, or a combination thereof). In one embodiment, the system 10 includes, but is not necessarily limited to, a laser 14 capable of generating a pulsed laser beam 18, an energy control module 16 for varying the pulse energy of the pulsed laser beam 18, a scanner 20 (e.g., a micro-optics scanning system), a controller 22, a user interface 32, an imaging system 34, and focusing optics 28 for directing the pulsed laser beam 18 from the laser 14 into the eye 12. The controller 22 communicates with the scanner 20 and/or focusing optics 28 to direct the focal point of the pulsed laser beam 18. Software (e.g., instrument software, and the like), firmware, or the like, can be executed by the controller 22 to command the actions and placement of the scanner 20 via a motion control system, such as a closed-loop proportional integral derivative (PID) control system. In this embodiment, the system 10 further includes a beam splitter 26 and a detector 24 coupled to the controller 22 to provide a feedback control mechanism for the pulsed laser beam 18. The beam splitter 26 and detector 24 may be omitted in other embodiments, for example, with different control mechanisms. To modify the in situ intraocular lens 30, the controller communicates with the scanner 20 and/or focusing optics 28 to direct the focal point of the pulsed laser beam 18 into the in situ intraocular lens 30 (i.e., sub-surface).

A variety of intraocular lenses may be implanted and modified in-situ by the system 10 including, but not necessarily limited to, monofocal intraocular lenses, multifocal intraocular lenses, accommodating intraocular lenses, and the like. Some intraocular lenses include, by way of example and not of limitation, the ReZoom™ multifocal lens, the Verisyse™ phakic lens, and the Tecnis® aspheric lens manufactured by Advanced Medical Optics, Inc., the AcrySof® ReStor®, AcrySof® IQ, and AcrySof Toric intraocular lenses manufactured by Alcon, Inc., and the Crystalens® intraocular lens manufactured by Bausch & Lomb, Inc. Some other examples of intraocular lenses are found in U.S. Pat. No. 5,571,177, which discloses intraocular lenses that are specifically structured to be post-operatively re-positioned. The system 10 modifies the intraocular lens 30 via photoalteration of one or more desired subsurface regions of the intraocular lens 30. Examples of photoalteration include, but are not necessarily limited to, chemical and physical alterations, chemical and physical breakdown, liquefaction, polymerization, disintegration, ablation, vaporization, or the like. Localized photoalterations can be placed at the targeted portion (i.e., in the desired subsurface region) of the intraocular lens 30 to provide high-precision processing. Where the pulsed laser beam 18 is directed (e.g, the focal point of the pulsed laser beam 18), the laser energy associated with the pulsed laser beam 18 modifies the material of the intraocular lens 30 and/or the mechanical properties associated therewith. For example, the mechanical properties associated with a specific component or portion of the intraocular lens 30 can be modified to have increased/decreased rigidity, increased/decreased viscoelasticity, increased/decreased flexibility, and the like. In another example, an intraocular lens with pre-stressed haptics can be treated by the system 10 to form slip zones in the haptics, thereby at least partially relieving the stress.

Different intraocular lenses or portions of a particular intraocular lens can have a variety of materials, each requiring different amounts of energy to effect a desired modification. For example, the optic and support element (e.g., a haptic) may each have different material compositions, and the support element may have different material compositions within different regions thereof (e.g., a non-homogeneous support element). The controller 22 preferably directs the energy control module 16, the scanner 20, or a combination of both, to produce a pulsed laser beam having sufficient energy to modify the intraocular lens material. For example, the energy control module 16 can vary the pulse energy in response to the controller 22 to produce the pulsed laser beam 18 with sufficient energy to modify the mechanical properties of subsurface regions of the haptic or a hinge or other structure coupling the haptic to the optic. Thus, the mechanical properties associated with the haptic or optic or both can be modified via the subsurface modifications to the intraocular lens 30. The spacing between adjacent pulses of the pulsed laser beam 18 can be varied, as well as the pulse repetition rate, spot size, and the like, to provide sufficient energy.

In one embodiment, the controller 22 directs the energy control module 16, the scanner 20, or a combination of both, to produce the pulsed laser beam 18 with pre-determined properties (e.g., corresponding with a specific intraocular lens or material) to modify the intraocular lens 30. Based on the physical characteristics of the intraocular lens to be implanted, the controller 22 selects pre-determined values of pulse energy, pulse width, pulse repetition rate, spot separation, or the like, or any combination thereof, to provide the energy for modifying the support element. For example, the specific type, brand, model, etc., of intraocular lens to be implanted may be input via the user interface 32. In response to this input information, one or more look-up tables are accessed by the controller 22 to retrieve the corresponding pre-determined values (e.g., to provide the appropriate energy for modifying the support element of the intraocular lens). For example, the entire intraocular lens or one or more portions of the intraocular lens may be formed from polymethylmethacrylate (PMMA). In this example, the look-up table contains an exposure time, a pulse energy value, a scan pattern, or the like, that corresponds with heating the subsurface region(s) above the glass transition temperature ($T_g$) associated with PMMA to modify the support element. By heating pre-determined subsurface regions of the support element above $T_g$, the support element is temporarily softened thereby allowing the support element to be bent, compressed, or otherwise altered from an original implanted state. The look-up tables can contain different pre-determined settings for a variety of materials, intraocular lens type, brand, model, etc., corresponding with the composition of the intraocular lens 30. Thus, a pulsed laser beam having the appropriate characteristics for modifying the subsurface regions of the intraocular lens 30 can be automatically produced by the system 10. The properties of the pulsed laser beam 18 may also be manually modified from default values (e.g., for a customized modification) or manually input by the operator as original operating values.

To provide the pulsed laser beam 18, the laser 14 utilizes a chirped pulse laser amplification system in one embodiment,—such as that described in U.S. Pat. No. RE37,585—, for photoalteration. U.S. Pat. Publication No. 2004/0243111 also describes other methods of photoalteration. Other devices or systems may be used to generate pulsed laser beams, including, by way of example and not limitation, the FS lasers manufactured by IntraLase Corp., the FEMTO LDV™ laser manufactured by Ziemer Ophthalmic Systems AG, the FEMTEC® laser by 20/10 Perfect Vision AG, and the VisuMax® laser manufactured by Carl Zeiss Meditec AG. For example, non-ultraviolet (UV), ultrashort pulsed laser technology can produce pulsed laser beams having pulse durations measured in femtoseconds. For example, U.S. Pat. No. 5,993,438, the entire disclosure of which is incorporated herein by reference, discloses an intrastromal photodisruption technique for reshaping the cornea using a non-UV, ultrashort (e.g., femtosecond pulse duration), pulsed laser beam that propagates through corneal tissue and is focused at a point below the surface of the cornea to photodisrupt stromal tissue at the focal point. In the system 10, the pulsed laser beam may be focused beyond the stromal tissue and into the capsular bag (e.g., to modify the intraocular lens 30).

The system 10 is capable of generating the pulsed laser beam 18 with physical characteristics similar to those of the laser beams generated by a laser system disclosed in U.S. Pat. No. 4,764,930, the entire disclosure of which is incorporated herein by reference, U.S. Pat. No. 5,993,438, or the like. For example, the system 10 can produce a non-UV, ultrashort pulsed laser beam for modifying the support element of the intraocular lens 30. The pulsed laser beam 18 preferably has laser pulses with durations as long as a few picoseconds or as short as a few femtoseconds. For intraocular photoalteration, the pulsed laser beam 18 has a wavelength that permits the pulsed laser beam 18 to pass through the cornea and the anterior chamber without absorption by either or with insignificant absorption. The wavelength of the pulsed laser beam 18 is generally in the range of about 3 μm to about 1.9 nm, preferably between about 400 nm to about 3000 nm, and is more preferably about 1053 nm.

The irradiance of the pulsed laser beam 18 for accomplishing photoalteration at the focal point is sufficient for the material associated with the support element. Although a non-UV, ultrashort pulsed laser beam is described in this embodiment, the laser 14 can produce a laser beam with other wavelengths in other embodiments. In one embodiment, the laser 14 preferably has a pulse repetition rate of about 150 kHz, although the laser 14 may operate at other pulse repetition rates (e.g., 30 kHz, 60 kHz, 120 kHz, and the like).

The focusing optics 28 direct the pulsed laser beam 18 toward the eye 12 (e.g., through the cornea and on or into the intraocular lens 30) for non-UV photoalteration of the subsurface regions within the intraocular lens 30. The system 10 may also include an applanation lens (not shown) to flatten the cornea prior to scanning the pulsed laser beam 18 into the eye 12. A planar, curved, or other shaped lens is used to contact the cornea.

The user interface 32 provides a flexible and simple environment for the operator to interact with the system 10. In one embodiment, the user interface 32 graphically displays (e.g., using a flat panel display or the like) information, such as from the instrument software controlling the operation of various components of the system 10, and provides a visual interface between the system 10 and the operator for inputting commands and data associated with the various components of the system. A graphical user interface (GUI) is preferably used with the user interface 32 employing menus, buttons, or other graphical representations that display a variety of selectable functions to be performed by the system 10 following selection. For example, the operator points to an object and selects the object by clicking on the object, touching a pre-designated region of a touch-screen displaying the GUI, or the like. Additional items may be presented on the GUI for operator selection, such as a button or menu item indicating an available sub-menu (e.g., a drop-down sub-menu). The user interface 32 may also utilize one or more of a variety of input devices including, but not necessarily limited to, a keyboard, a trackball, a mouse, a touch-pad, a touch-sensitive screen, a joystick, a variable focal length switch, a footswitch, and the like.

In addition to the user interface 32, the imaging system 34 displays a magnified real-time digital image of the eye 12 (e.g., a front view) and provides an interface for viewing the eye 12, including various structures thereof, and operator control of the centration or alignment of the laser output with the eye 12. In one embodiment, an alignment or centration aid is displayed by the imaging system 34 overlaying the digital image of the eye 12. The aid corresponds with the position of the laser output in reference to the eye 12. As part of the photoalteration process, the output of the laser 14 is preferably aligned with the eye 12 (e.g., the center of the pupil, the center of the outer boundary of the iris, and the like) and/or the intraocular lens 30. For example, the output of the laser 14 is substantially centered with reference to the pupil and iris of the eye 12. In another example, the output of the laser 14 is substantially centered with reference to the optic portion of the intraocular lens 30 (e.g., along a central optical axis of such optic portion). Viewing the digital image displayed by the imaging system 34, the operator can center the aid (e.g., based on the pupil and/or the iris of the patient's eye and/or the intraocular lens) and adjust the position of the laser output.

After alignment or centration, the system 10 directs the pulsed laser beam 18 at the support element of the intraocular lens 30 implanted in the eye 12. Movement of the focal point of the pulsed laser beam 18 is accomplished via the scanner 20 in response to the controller 22. The step rate at which the focal point is moved is referred to herein as the scan rate. The term "scan" or "scanning" refers to the movement of the focal point of the pulsed laser beam along a desired path or in a desired pattern. For example, the scanner 20 can operate at scan rates between about 10 kHz and about 400 kHz, or at any other desired scan rate. Further details of laser scanners are generally known in the art, such as described, for example, in U.S. Pat. No. 5,549,632, the entire disclosure of which is incorporated herein by reference.

In one embodiment, the scanner 20 utilizes a pair of scanning mirrors or other optics (not shown) to angularly deflect and scan the pulsed laser beam 18. For example, scanning mirrors driven by galvanometers are employed where each of the mirrors scans the pulsed laser beam 18 along one of two orthogonal axes. A focusing objective (not shown), whether one lens or several lenses, images the pulsed laser beam 18 onto a focal plane of the system 10. The focal point of the pulsed laser beam 18 is thus scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis. Any combination of scanning along one or more of these axes may be used to direct the focal point of the pulsed laser beam 18 into the intraocular lens 30.

The controller 22 can access an updateable database of scanning routines to modify the subsurface region(s) of the intraocular lens 30. In one embodiment, each of the scanning routines corresponds to a particular type of intraocular lens and provides a selection of pre-programmed scanning instructions to affect a variety of modifications. For example, for a specific intraocular lens type, a scanning routine accounts for the lens dimensions, material properties, surface shapes, and the like, associated with the lens. The scanning instruction can include pre-identified subsurface locations within the particular intraocular lens, or sets of locations, that correspond with increasing/decreasing flexibility of a support element (e.g., a hinge or a haptic), increasing/decreasing viscoelasticity of a portion of the intraocular lens, creating one or more slip zones at pre-determined subsurface regions, or altering a variety of other mechanical or structural properties of a desired portion of the intraocular lens. Each of the pre-programmed scanning instructions can be manually modified via the user interface 32 as well, such as for customization.

For example, in one embodiment, an image of the eye illustrating the locations of various anatomical structures of the eye as well the intraocular lens 30 location can be displayed on a touch-sensitive screen of the user interface 32. For a particular intraocular lens type and desired modification, the user interface 32 displays the locations of the subsurface regions to be scanned by the pulsed laser beam 18. The operator can modify the locations of the subsurface regions using an input device, such as a stylus, and drawing on the touch-sensitive screen a change from the illustrated subsurface regions to a modified subsurface location. In another embodiment, the operator indicates the desired subsurface regions on the touch-sensitive screen, and the controller 22 determines a corresponding scanning procedure for directing the pulsed laser beam 18 at the subsurface regions.

In another embodiment, the operator can indicate a desired mechanical movement of a portion of the intraocular lens on the touch-sensitive screen (e.g., via a drawn arrow on the touch-sensitive screen indicating a displacement along the direction of the arrow). An image recognition application may be used by the controller 22 to identify the desired mechanical movement from the drawn arrow, and the controller 22 can then determine and propose subsurface regions (e.g., displayed on the user interface 32) to be scanned corresponding to the desired mechanical movement. For example, the operator can indicate a desired shift in position (e.g., a shift along the x- and/or y-axis, a shift along the z-axis, a tilt, a rotation, and the like) of the optic or intraocular lens as a whole (e.g., to establish the proper power provided by the intraocular lens, fine tune the refractive correction, and the like). One or more slip zones can also be drawn or otherwise indicated by the operator on the user interface 32 (e.g., via the touch-sensitive screen), and the controller 22 then determines the scanning procedure to produce the slip zones.

For further customization, the system 10 acquires detailed information about optical aberrations to be corrected, at least in part, using the system 10. These aberrations are determined prior to implantation of the intraocular lens 30, at a time subsequent to the implantation of the intraocular lens 30 (e.g., after the settling period following implantation), after further ophthalmic procedures (e.g., LASIK or other corneal corrections, intracorneal modifications such as intracorneal implants, and the like) have been performed, or concurrently with the procedure for modifying the intraocular lens 30. Examples of such detailed information include, but are not necessarily limited to, the desired correction, the actual correction (e.g., measured), the re-orientation of the intraocular lens, and the like.

The refractive power of the cornea with or without corrections made thereto (e.g., prior ophthalmic procedures such as flap creation, LASIK, photorefractive keratectomy (PRK), laser assisted sub-epithelium keratomileusis (LASEK), corneal pocket creation, corneal transplant, and the like) may be used to determine initial refractive corrections and/or additional corrections. Wavefront analysis techniques, made possible by devices such as a Hartmann-Shack type sensor (not shown), can be used to generate maps of corneal refractive power. Other wavefront analysis techniques and sensors may also be used. The maps of corneal refractive power, or similar refractive power information provided by other means, such as corneal topographers, optical coherence tomography scanners, pachymeters, and the like, can then be used to identify and locate optical aberrations of the cornea that require correction. Determination of the particular subsurface regions within the intraocular lens for alteration (e.g., mechanical or structural alteration via the pulsed laser beam 18) can be based on the refractive power map or other optical modeling of the patient's eye. In one embodiment, real-time wavefront analysis is used as a feedback mechanism for guiding the intraocular lens modifications. This wavefront analysis may be concurrently displayed on the user interface 32 or as a separate image together with the image of the eye and intraocular lens to substantially indicate the effects of the modifications in real-time (e.g., the wavefront analysis represents in real-time the optical effects associated with the intraocular lens modifications, re-orientations, and the like).

Figure 2:
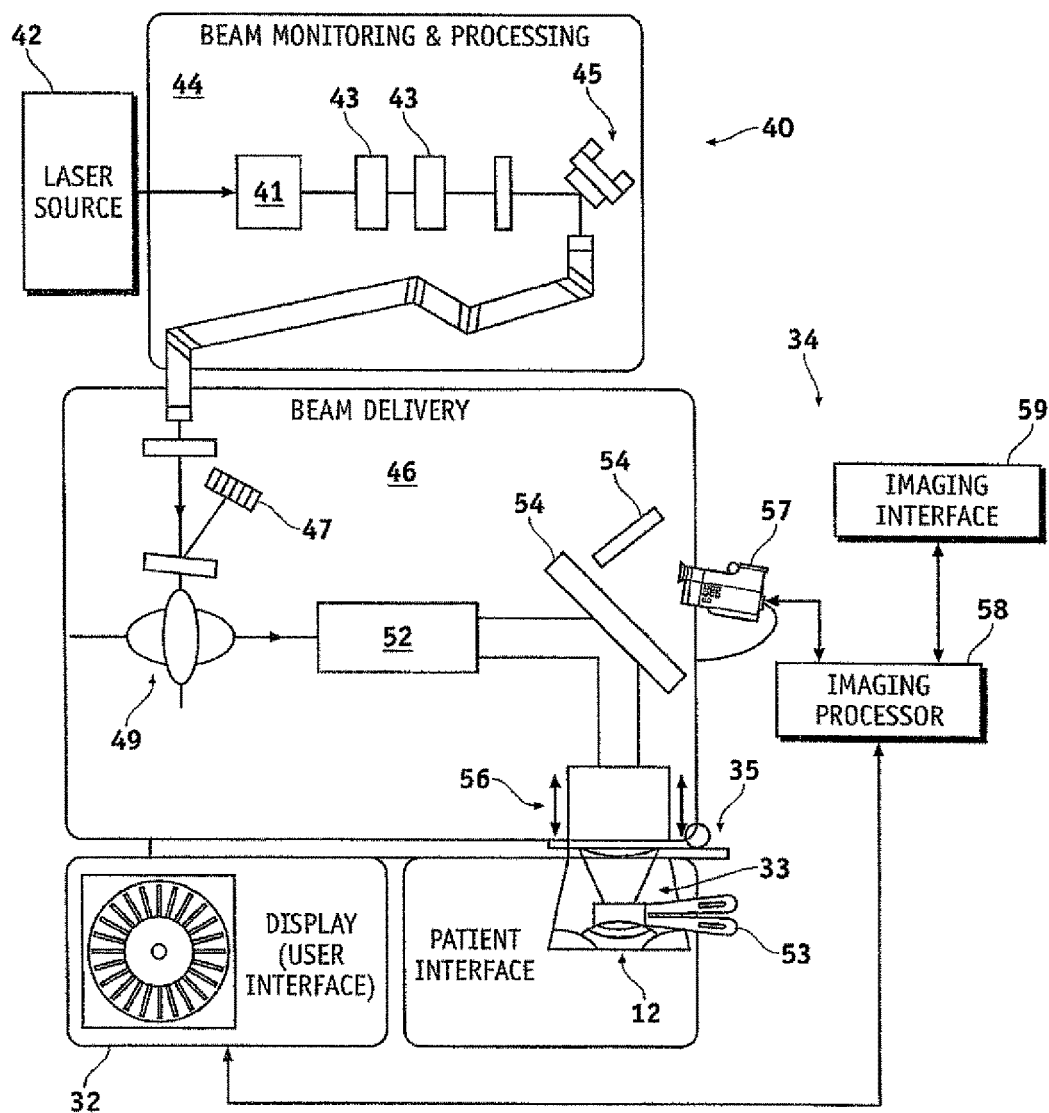
FIG. 2 is a block diagram of an ophthalmic laser system in accordance with one embodiment.

FIG. 2 is a block diagram of an ophthalmic laser system 40 in accordance with one embodiment of the present invention. Referring to FIGS. 1 and 2, the ophthalmic laser system 40 includes, but is not necessarily limited to, a laser source 42 providing a pulsed laser beam (e.g., the pulsed laser beam 18), a beam monitoring and processing module 44, a beam delivery module 46 coupled to the beam monitoring and processing module 44, the user interface 32, and the imaging system 34. Although described as a single system, one or more components of the system 40 may be self-contained separate subsystems that are coupled together to form the system 34. The pulsed laser beam is supplied to the beam monitoring and processing module 44 where the pulse energy, the focal point separation, and optionally the minimum sub-surface depth of the pulsed laser beam are controlled. For example, a beam splitter (not shown), such as the beam splitter 26, can be used to provide a feedback loop for the pulsed laser beam 18 to the beam monitoring and processing module 44. The beam delivery module 46 scans the pulsed laser beam along a desired scan region (e.g., as determined by the controller 22). In this embodiment, the ophthalmic laser system 40 can be coupled to the eye 11 via a patient interface 33, and the patient interface 33 may be coupled to the ophthalmic laser system 40 at a moveable loading deck 35, for example. The configuration of the ophthalmic laser system 40 may vary as well as the organization of the various components and/or sub-components of the ophthalmic laser system 40. For example, some components of the beam delivery module 46 are incorporated with the beam monitoring and processing module 44 and vice versa.

The user interface 32 is coupled to the beam delivery module 45, and a variety of system parameters may be input or modified by the operator via the user interface 32 to control the beam properties and thus produce the desired photoalteration. For example, the user interface 32 includes a display presenting a graphical user interface with the various system parameters and an input device (not shown) for selecting or modifying one or more of these parameters. The number and type of system parameters may vary for modifying a particular intraocular lens (e.g., pulse energy, spot size, spot shape, focal point separation, focal point depth, scanning pattern, scanning sequence, scan rate, and the like). While described for modifying intraocular lenses, the system 40 may be used for a variety of other ophthalmic procedures (e.g., flap creation, PRK, LASIK, LASEK, corneal pocket creation, corneal transplant, corneal implant, corneal inlay, and the like), and additional system parameters may be provided by the user interface 32 for such other procedures.

In one embodiment, the parameters are input, selected, or modified by the operator via the user interface 32. For intraocular lens modification, the operator is prompted via the user interface 32 with the selection of parameters. The parameters may be displayed as default values for selective modification by the operator. Additional parameters may also be displayed by the user interface 32 for different procedures using the system 40.

In response to the system parameters selected or input via the user interface 32, the beam monitoring and processing module 44 and/or the beam delivery module 46 produce a pulsed laser beam with properties corresponding with the system parameters. In one embodiment, the beam monitoring and processing module 44 includes, but is not necessarily limited to, an energy attenuator 41, one or more energy monitors 43, and an active beam positioning mirror 45. The pulsed laser beam is directed from the laser source 42 to the energy attenuator 41, then to the energy monitor 43, and then to the active beam positioning mirror 45. The active beam positioning mirror 45 directs the pulsed laser beam from the beam monitoring and processing module 44 to the beam delivery module 46. Using the energy attenuator 41 and energy monitor 43, the pulse energy of the pulsed laser beam may be varied to desired values. Additionally, the spatial separation of the focal points of the pulsed laser beam may be varied by the beam monitoring and processing module 44. This is particularly useful to increase the precision associated with a desired modification of the intraocular lens 30 (e.g., to create a slip zone within the intraocular lens with pre-determined dimensions corresponding to a desired displacement or actuation).

The beam delivery module 46 scans the pulsed laser beam at the desired subsurface region of the intraocular lens 30. In one embodiment, the beam delivery module 46 includes, but is not necessarily limited to, a beam position monitor 47, an x-y scanner 49, a beam expander 52, one or more beam splitters 54, and a z-scanning objective 56. The pulsed laser beam is received from the beam monitoring and processing module 44 by the x-y scanner 49 and directed to the beam expander 52, and the beam expander 52 directs the pulsed laser beam to the z-scanning objective via the beam splitter (s) 54. The z-scanning objective 56 can vary the focal point depth of the pulsed laser beam (e.g., from the anterior surface of the eye 12 or cornea to any depth within the eye 31 up to and including the retinal region). For modifying the intraocular lens 30, the z-scanning objective 56 preferably directs the focal point of the pulsed laser beam to the depth of the intraocular lens 30 within the lens capsule bag.

Prior to initiating scanning or otherwise initiating photoalteration of the intraocular lens 30, the eye 12 is preferably substantially immobilized with respect to the ophthalmic laser system 40 (e.g., the ophthalmic laser system 40 can be coupled to the eye 12). In one embodiment, the patient interface 33 provides a surface for contacting the cornea of the patient's eye 12, which may also be used to applanate the cornea. A suction ring assembly 53 or other device may be applied to the eye 12 to fixate the eye prior to coupling the ophthalmic laser system 40 to the eye (e.g., via the patient interface 33). In one embodiment, the suction ring assembly 53 has an opening providing access to the eye 12 when coupled thereto. The imaging system 34 may be used to facilitate the coupling of the ophthalmic laser system 40 with the eye 12. For example, by providing a real-time image of the fixated eye, the operator can view the eye to properly center the output of the beam delivery module 46 (e.g., with respect to the pupil, the iris, the pupil and the iris, any other features of the eye 12, the intraocular lens 30, or any structure of the intraocular lens 30).

Once the ophthalmic laser system 40 is coupled to the eye 12, the imaging system 34 may be used for alignment or centration of the laser output (e.g., the beam delivery module 46 output) and/or applanation of the cornea using the patient interface 33. A variety of centration and alignment devices or methods (e.g., two-dimension alignment, such as x- and y-axis, or three-dimension alignment, such as x-, y-, and z-axis) may also be used with the imaging system 34 to couple the system 40 with the eye 12. The imaging system 34 preferably provides a real-time, magnified, high resolution digital image of the eye 12 and includes, but is not necessarily limited to, an image sensor 57, an imaging interface 59, and an image processor 58 coupled to the sensor 57 and the interface 59. An image of the eye 12, as well as the intraocular lens 30, is captured using the image sensor 57 and displayed by the imaging interface 59. In one embodiment, a high resolution digital camera (e.g., a high-definition digital video camera based on charge coupled devices (CCDs) or the like) is used to capture the image and display the image on the imaging interface 59.

Although FIG. 2 illustrates a combination of the image sensor 57 and beam splitters 54 for capturing the image, the image sensor 57 may be located in a variety of different positions or operate solely or operate with additional optical elements to directly or indirectly capture images of the eye 12. For example, the image sensor 57 may be located substantially adjacent to the z-scanning objective 56 to directly capture images of the eye 12. In one embodiment, the image sensor 57 is mounted on a moveable gantry to vary the image focal plane captured by the image sensor 57 and optically coupled with a variable aperture (not shown) (e.g., positioned between the image sensor 57 and the eye 12) for controlling the depth of focus and/or the amount of light sensed by the image sensor 57. In another embodiment, at least one or more of a focus control for varying the image focal plane captured by the image sensor 57 and a focus depth control are incorporated into the image sensor 57. This is useful for focusing onto an optical plane associated with the intraocular lens 30, particularly in instances when greater resolution is desired than associated with the depth of focus.

The imaging interface 59 includes, but is not necessarily limited to, an input device for operator selection of system parameters (e.g., associated with coupling the ophthalmic laser system 40 with the eye 12, modification of the desired subsurface regions of the intraocular lens 30, image control, and the like) and a monitor displaying the real-time, magnified, high resolution digital image of the eye 12, various structures of the eye 12, the intraocular lens 30 implanted within the eye 12, and the like. The input device includes one or more of a keyboard, a trackball, a mouse, a touch-pad, a touch-sensitive screen, a joystick, a variable focal length switch, a footswitch, and the like. In a preferred embodiment, the imaging interface 59 includes a touch-sensitive screen displaying a graphical user interface for selecting the system parameters and for viewing the eye 12, the intraocular lens 30, the alignment or centration of the laser output with reference to the eye 12, pre-determined or selected subsurface regions of the intraocular lens, and the like. The graphical user interface provides a variety of buttons, icons, or the like corresponding with different functions for selection by the operator, and the operator selects a particular function by touching the corresponding button displayed on the touch-sensitive screen.

Operator control of the beam delivery module 46 alignment with the eye 12 or intraocular lens 30, applanation of the cornea, and/or centration is provided via the input device of the imaging interface 59 or via a separate input device (e.g., a joystick). For example, the operator controls the raising, lowering, or lateral movement (two-dimensions) of the loading deck 35 with the joystick while viewing the digital image of the eye 12 provided by the imaging system 34. The operator can adjust the lateral position (e.g., an x-axis position and a y-axis position) of the loading deck 35 to align the output of the beam delivery module 46 with the eye 12 and lower the loading deck 35 (e.g., along a z-axis) to guide the patient interface 33 into a pre-determined position with the suction ring 53 (e.g., coupling the beam delivery module 46 with the eye 12). An indicator may also be displayed by the imaging interface 59 (e.g., a green light) when the beam delivery module 46 is properly coupled with the eye 12 or when an applanation surface of the patient interface 33 contacts the cornea. The operator then applanates the cornea by further lowering the beam delivery module 46 (e.g., the loading deck 35 and patient interface 33) using the input device, while monitoring the degree of applanation as indicated by the digital image of the eye 12, and discontinuing movement of the beam delivery module 46 at a desired degree of applanation determined by viewing the digital image of the eye 12.

In one embodiment, a centration aid is displayed as an overlay on the digital image of the eye 12 for assisting in centering the laser output with the eye 12 or the intraocular lens 30. The centration aid corresponds with the current position of the laser output with reference to the eye 12 or the intraocular lens 30 (e.g., the two-dimensional position in the focal plane of the pulsed laser beam and/or axial alignment of the pulsed laser beam with reference to an optical axis of the eye 12 or intraocular lens 30). The operator can align or center the laser output using the joystick, or other input device, together with the centration aid. For example, by centering the centration aid with reference to the image of the pupil, the iris, the intraocular lens 30, or any combination thereof, displayed by the imaging interface 59, the output of the beam delivery module 46 becomes centered with reference to the pupil, the iris, both the pupil and iris, the optic of the intraocular lens, or any structure of the intraocular lens or the eye. Following alignment or centration, the operator can initiate scanning and photoalteration of the desired subsurface region(s) of the intraocular lens (e.g., within the haptic, the optic, or both the haptic and optic).

Figure 3:
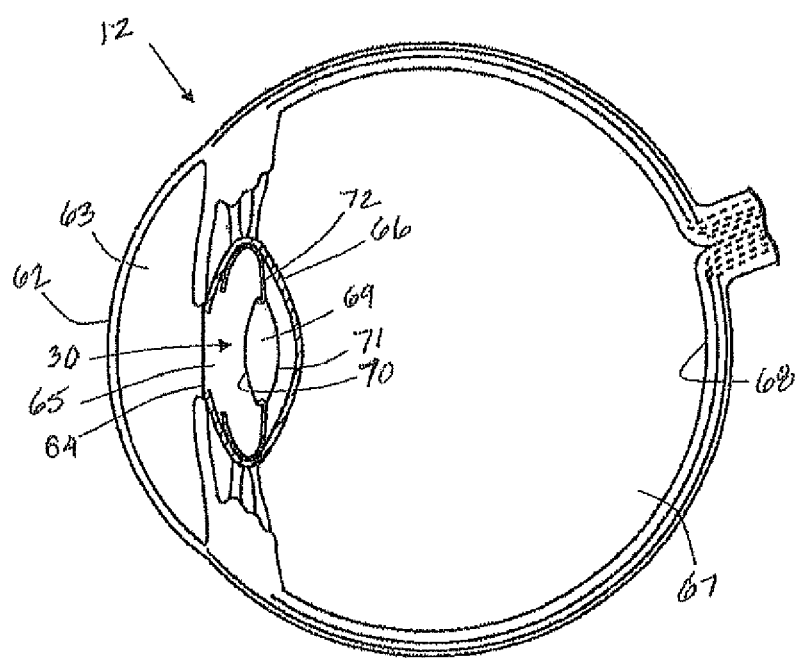
FIG. 3 is a schematic drawing of the human eye with the implanted intraocular lens shown in FIG. 1.

FIG. 3 is a cross-sectional view of the human eye 12 with the implanted intraocular lens 30, shown in FIG. 1. Light enters from the left of FIG. 3, and passes through the cornea 62, the anterior chamber 63, the iris 64, and enters the capsular bag 65. The intraocular lens 30 replaces the natural lens of the eye 12. Prior to surgery, the natural lens occupies essentially the entire interior of the capsular bag 65. After surgery, the capsular bag 65 contains the entire intraocular lens 30, in addition to a fluid (not shown) that occupies the remaining volume (e.g., unoccupied by the intraocular lens 30) and equalizes the pressure within the eye 60. After passing through the intraocular lens 30, light exits a posterior wall 66 of the capsular bag 65, passes through a posterior chamber 67, and strikes the retina 68, which detects and converts the light to a signal transmitted through the optic nerve to the brain.

The intraocular lens 30 has an optic 69 with a refractive index greater than the fluid surrounding the intraocular lens 30. The optic 69 has an anterior surface 70 facing away from the retina 68 and a posterior surface 71 facing toward the retina 68. The optic 69 is held in place by a positioning member 72 (e.g., a haptic), which couples the optic 69 to the capsular bag 65. In this embodiment, the optic 69 is suspended within the capsular bag 65 to allow accommodative movement of the optic 69 of the intraocular lens 30 along the optical axis, for example. In another embodiment, the intraocular lens 30 is disposed adjacent to, and even pressed against, the posterior wall 66, for example, to reduce cellular growth on the optic 69. The optic 69 can also be a monofocal intraocular lens or a multifocal intraocular lens.

A well-corrected eye typically forms an image at the retina 68. If the lens has too much or too little power, the image generally shifts axially along the optical axis away from the retina 68 and toward or away from the lens. Note that the power associated with focusing on a close or near object is more than the power associated with focusing on a distant or far object. The difference in optical power between the farthest and nearest object that may be brought into focus by a particular lens or lens system is commonly referred to as an "add power" (e.g., in the case of a multifocal intraocular lens) or a "range of accommodation" or "accommodative range" (e.g., in the case of an accommodating intraocular lens that responds to ciliary muscle contraction to move and/or deform axially and thereby change the optical power of the corresponding optic). A normal add power or accommodation is about four (4) Diopters at the plane of the optic 69 of an intraocular lens, although this number may be three (3) or fewer Diopters or six (6) or more Diopters, depending on the geometry of the particular eye.

An accommodating intraocular lens, such as those disclosed in U.S. Patent Application Publication Number 2004/0111153 (Woods et al.), or in U.S. Pat. No. 7,713,299 (Brady et al.) and U.S. Patent Application Publication Number 2008/0161914 (Brady et al.), all of which are herein incorporated by reference in their entirety, may be used as the intraocular lens 30. For example, the optic 69 has a clear aperture that is disposed about a central axis or optical axis (OA). The optic is configured to change shape in response to an ocular force, thereby changing the optical power of the optic by at least about one (1) Diopter, preferably by at least two (2) Diopters, three (3) Diopters, or four (4) Diopters. For example, the optic may be made of a relatively soft material such as a soft acrylic or silicone material having a modulus of less than about 100 kPa or less than about 50 kPa. As used herein, the term "ocular force" refers to a force produced by the eye for accommodation, for example, a force produced by the ciliary muscle, zonules, or capsular bag of the eye. Alternatively or additionally, the optic 69 may be configured to produce an effective change in the optical power of the optic by displacing the optic along the optical axis OA in response to an ocular force. The positioning member 72 is generally flexible and configured for changing the shape of the optic 69 in response to the ocular force.

The intraocular lens 30 is generally configured to be placed within the capsular bag of the eye and configured to be compressed to provide near or intermediate vision and/or stretched to provide distant vision. In another embodiment, the optic 69 may further include a mask (not shown) having a mask profile that is imposed on, added to, or combined with the shape of a base surface of the optic. The mask includes a diffractive or refractive surface with a relatively low add power in another embodiment. For example, a low add power of less than about two (2) Diopters, or even less than one (1) Diopter, may be used to increase the depth of focus of the intraocular lens when in one or more states of accommodation, thereby reducing the amount of deformation or displacement necessary to provide a predetermined amount of accommodation. In another embodiment, the diffractive surface is replaced with or added to a surface profile incorporating one or more of the other configurations discussed herein to provide extended or enhanced depth of focus.

The ocular force applied to the intraocular lens 30 is generally provided directly by the capsular bag into which the intraocular lens is placed. In another embodiment, the positioning member 72 is configured so that the ocular force used to deform the optic 69 is provided more directly by the ciliary muscle and/or zonules, for example, by removing the capsular bag or placing the intraocular lens in front of the capsular bag. In any case, the intraocular lens 30 is generally configured to provide a predetermined amount of accommodation when the ciliary muscle contracts and/or relaxes and with an ocular force of less than about twenty (20) grams, less than about ten (10) grams, or even less than about five (5) grams.

The intraocular lens 30 is configured to have a predetermined ocular power when in a reference state, for example, with substantially no external forces on the intraocular lens 30, except for gravity. In some embodiments, while there is substantially no external force on the intraocular lens 30 when in the reference state, the intraocular lens experiences internal forces, for example, produced between the optic 69 and the positioning member 72 due to a pre-stress introduced during fabrication. The optical power of the intraocular lens 30, when in the reference state, is selected to provide near vision (an accommodative bias), distant vision (a dis-accommodative bias), or intermediate vision.

The positioning member 72 may also be configured to additionally translate the intraocular lens 30 along the optical axis in the anterior direction (e.g., toward the cornea) to further enhance the accommodative power of the intraocular lens 30. In other embodiments, the positioning member 72 is replaced by a positioning member particularly suited for providing accommodative motion along the optical axis OA, for example, a positioning member configured like or similar to those disclosed in U.S. Patent Application Numbers 2004/0082993, 2004/0111153, or 2006/0253196, all of which are herein incorporated by reference.

A diffractive or refractive multifocal lens may also be used for the intraocular lens 30. For example, the optic 69 can have an anterior surface with a first shape, an opposing posterior surface with a second shape, and a multifocal element or pattern imposed on, added to, or combined with the second shape. The first and second surfaces together providing a base power and an add power, and the add power generally results from an add power associated with the multifocal element. In certain embodiments, the add power or effective add power of the optic 69 is produced by a combined effect of both the anterior and posterior surfaces. For example, a mask with an add power can be combined with an add power of the multifocal element to produce a total or effective add power of the optic 69. Alternatively, the profile of the mask differently affects a base power and an add power of the multifocal element to produce an add power of the optic 410 that is higher or lower than the power of the multifocal element alone.

In one multifocal embodiment, the anterior and posterior surfaces are configured to produce a first focus and a second focus when the optic 69 is placed within the eye. The first focus corresponds to or is produced by the base power of the optic 69 and generally provides a subject with distant vision. The second focus corresponds or is produced by the add power of the optic 69 and generally provides a subject with near or intermediate vision. As used herein, the term "near vision" refers to focusing on objects or planes that are relatively close to the subject, generally within a range of about 25-40 cm or at a distance at which a subject would generally place printed material for the purpose of reading. As used herein the term "intermediate vision" refers to focusing on objects situated approximately 40 centimeters to approximately 1.5 meters from the eye or a spectacle plane. As used herein, the term "distant vision" refers to focusing on objects or planes that are relatively distant from the subject, for example, generally at a distance that is greater than about 1 meter to about 2 meters away from the subject or at a distance of 5 to 6 meters or greater.

The base power and the add power are generally powers of the optic when the lens is disposed within a medium having a refractive index similar to that of the aqueous humor of the eye, for example, in a medium having a refractive index of or about 1.336. In other embodiments, the reference media is different from the media of the aqueous humor, for example, a refractive index of air or about 1.

The multifocal element can be a diffractive element in which two or more diffractive orders are used to provide two or more optical powers. Alternatively or additionally, the multifocal element is a refractive multifocal, for example, as disclosed in U.S. Pat. Nos. 5,225,858 or 6,210,005, which are incorporated in their entirety herein. In some embodiments, the multifocal element has a relatively low add power (e.g., less than about or equal to 2 Diopters or less than or equal to about 1 Diopter), for example, with a diffractive pattern. In such embodiments, the relatively low add power of the multifocal element can be combined with a multifocal element on the anterior surface to produce a combined add power of the optic that has a predetermined value. In other embodiments, the multifocal element has a relatively high add power (e.g., greater than or equal to about 3 Diopters or greater than or equal to about 4 Diopters), for example, so that the intraocular lens provides two or more distinct foci when placed in the eye of a subject (e.g., to one for near vision and another for distant vision).

The system 10, 40 may be used to modify the structure of the intraocular lens 30 following implantation/insertion into the eye. In one embodiment, material from the intraocular lens 30, such as on or in the positioning member 72, is ablated or photoaltered (e.g., by the pulsed laser beam produced by the system 10, 40). For example, void areas within the positioning member 72 are produced to weakened specific zones within the positioning member 72. In general, the pulsed laser beam produced by the system 10, 40 (e.g., using a laser with an ultra-short pulse in the picosecond to femtosecond range, such as an Nd:YLF laser operating at a wavelength of about 1053 nm) does not produce heat sufficient to impair the eye. The system 10, 40 may thus be focused to produce a condition of laser-induced optical breakdown, which produces an insignificant amount of heat.

In one embodiment, an accommodating intraocular lens has an optic and a positioning member or support structure with multiple arms, and each of the arms has a hinge area about which the arm can pivot and provide accommodative motion of the optic. For implantation/insertion (e.g., through a relatively narrow conduit), the hinges may be configured with substantial stiffness to withstand transportation through the narrow conduit. For example, the hinges are formed of a material having a desired stiffness or relative inflexibility. Following implantation/insertion, the hinges are biomechanically altered by the system 10, 40 to allow a more efficient transfer of ocular forces (e.g., from the ciliary muscle) into axial motion of the optic. In one example, the system 10, 40 precisely directs the pulsed laser beam at the hinges to create sub-surface slip zones, which enhance the accommodative effect of the intraocular lens.

In another embodiment, the accommodating intraocular lens is implanted into the eye and includes a haptic of photosensitive polymer material that is partially polymerized. The partially polymerized haptic is more compliant for transport through the narrow conduit. Following implantation/insertion, the system 10, 40 can be used to direct the pulsed laser beam into the haptic to extend polymerization of the haptic until a pre-determined stiffness is achieved (e.g., a stiffness suited to the transfer of energy to the intraocular lens for accommodative motion and/or deformation of the optic).

In yet another embodiment, the intraocular lens includes an optic and a support structure that are separately implanted into the eye. Alternatively, the optic and support structure are partially coupled to one another for a more compact configuration of the intraocular lens during implantation/insertion into the eye. Following implantation/insertion of both structures, the system 10, 40 can direct the pulsed laser beam to join or weld portions of the optic to the support structure.

The pulsed laser beam produced by the system 10, 40 may also be used to fit the implanted intraocular lens 30 to the capsular bag 65 or other structure. For example, the support structure can be weakened, expanded, or rearranged to fit the intraocular lens to the capsular bag. This is particularly useful for enhancing or optimizing an accommodative effect of a suitably configured intraocular lens.

Figure 4:
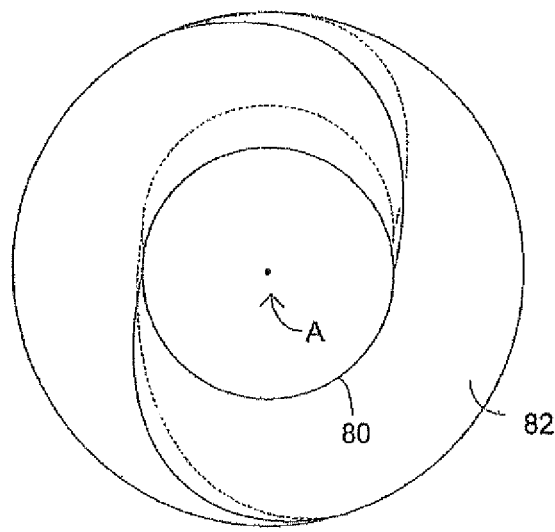
FIG. 4 is a top sectional view of an implanted intraocular lens illustrating a re-orientation in accordance with one embodiment.
Figure 5:
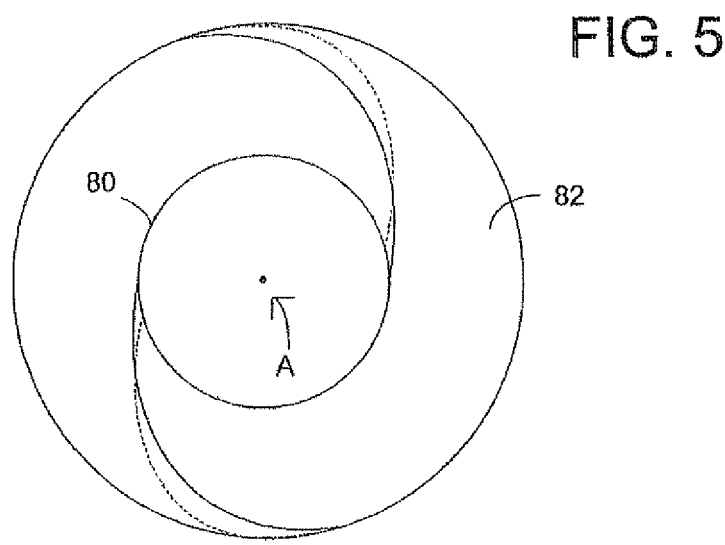
FIG. 5 is a top sectional view of the implanted intraocular lens illustrating a re-orientation in accordance with another embodiment.
Figure 6:
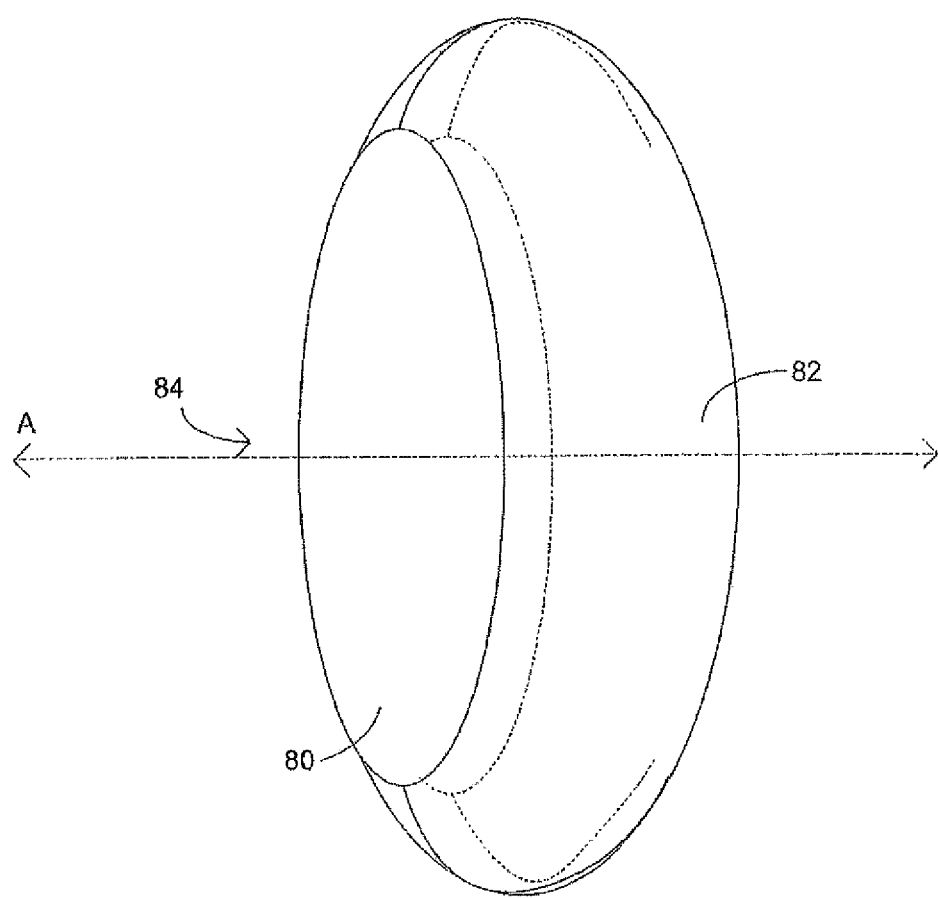
FIG. 6 is a side sectional view of the implanted intraocular lens illustrating a re-orientation in accordance with another embodiment.

As previously mentioned, a variety of re-orientations (e.g., displacements horizontally, vertically, diagonally, rotationally, non-linearly, combinations of one or more of the foregoing, and the like) are possible using the system 10, 40. FIG. 4 is a top sectional view of an implanted intraocular lens 80 illustrating a re-orientation in accordance with one embodiment. FIG. 5 is a top sectional view of the implanted intraocular lens 80 illustrating a re-orientation in accordance with another embodiment. FIG. 6 is a side sectional view of the implanted intraocular lens 80 illustrating a re-orientation in accordance with another embodiment. The intraocular lens 80 is implanted within the capsular bag 82 of an eye, such as the eye 12 shown in FIGS. 1 and 2. In these embodiments, the intraocular lens 80 is re-oriented from an initial position (in broken line) to the final position illustrated in FIGS. 4-6. The final position is substantially aligned (e.g., centered) with reference to an optical axis, A, of the eye. The system 10, 40 (FIGS. 1 and 2) may be used for these re-orientations as well as for a variety of other re-orientations of an in situ intraocular lens. As shown in FIG. 4, the intraocular lens 80 is translated along the horizontal axis or a y-axis to center the intraocular lens 80 about the optical axis or another selected axis. As shown in FIG. 5, the intraocular lens 80 is rotationally re-oriented about the optical axis. As shown in FIG. 6, the intraocular lens 80 is re-oriented along the optical axis or a z-axis to vault the intraocular lens 80 against the posterior portion 84 of the capsular bag 82.

Although the final position of the intraocular lens 80 is substantially aligned with reference to the optical axis, the intraocular lens 80 may be aligned based on other references, including the pupil or macula, for example. Using real-time wavefront analysis or other refractive analysis techniques of the eye for feedback input, the system 10, 40 can also indicate (e.g., via the user interface 32 shown in FIG. 1) the relative change to the refractive profile of the eye during re-orientation as well as subsequent to re-orientation of the intraocular lens 80.

Figure 7:
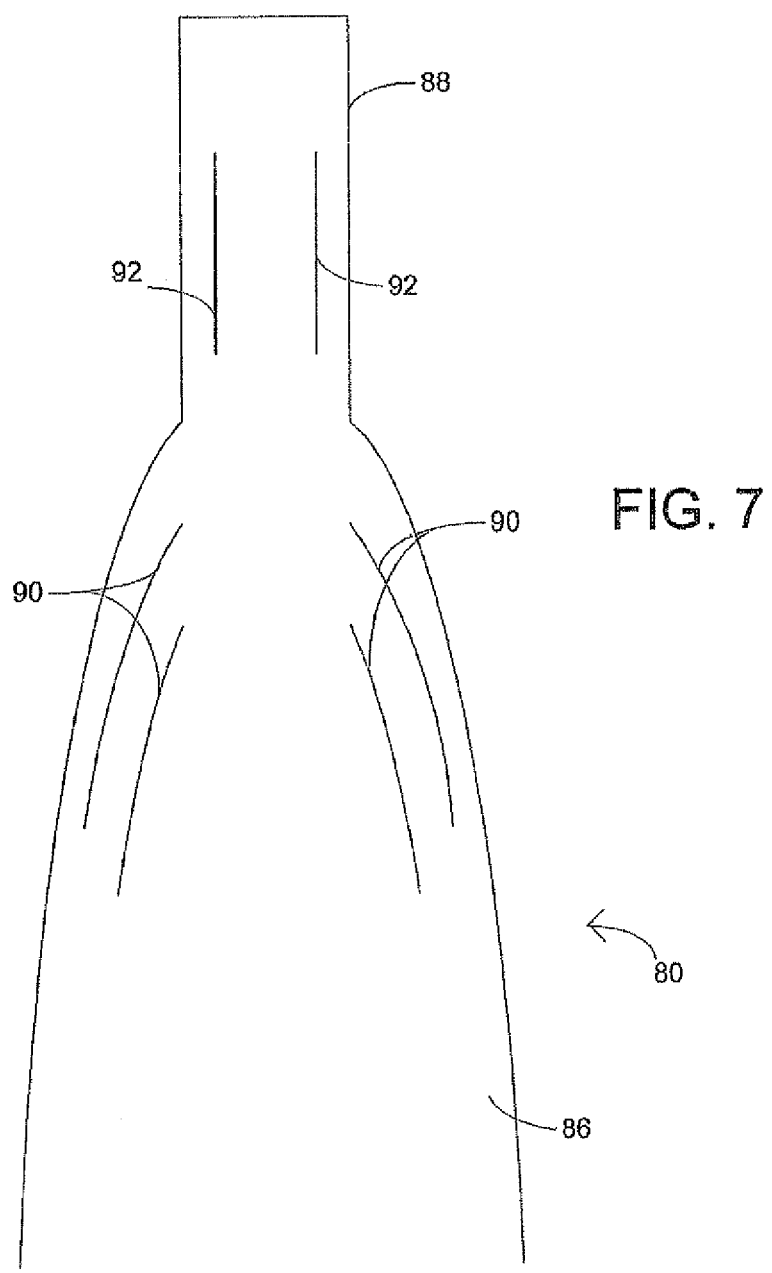
FIG. 7 is a sectional view of an intraocular lens illustrating slip zones in accordance with one embodiment.

FIG. 7 is a sectional view of the intraocular lens 80 illustrating slip zones 90, 92 in accordance with one embodiment. The intraocular lens 80 includes an optic portion 86 and a haptic portion 88, and the slip zones 90, 92 are located in pre-determined sub-surface regions of the intraocular lens 80 to induce a modification to the mechanical or structural characteristics thereof. The system 10, 40 (FIGS. 1 and 2, respectively) may be used to form the slip zones 90, 92. In this embodiment, some slip zones 92 are formed in the haptic portion 88 or in a hinge coupling the haptic portion 88 to the optic portion 86, and some slip zones 90 are formed in the optic portion 86. With the slip zones 92, the flexibility of the haptic portion 88 as a whole may be temporarily or permanently altered, and this feature can facilitate a re-orientation of the intraocular lens 80. For example, the slip zones 92 can increase flexibility of the haptic portion 88 to allow displacement of the position of the optic portion 86 (e.g., anterior or posterior vaulting, rotation, tilt, linear shift, and the like) and to more precisely or more accurately implement the refractive correction provided by the intraocular lens 80. The intraocular lens 80 may also be engineered with various structural elements that have been pre-determined to facilitate a desired re-orientation (e.g., along a specific displacement vector). In another example, the slip zones 92 are formed prior to implantation (e.g., during manufacture or finishing of the intraocular lens 80) to increase flexibility of the haptic portion 88 and ease folding or insertion of the intraocular lens 80.

The slip zones 90 formed in the optic portion 86 may also assist in re-orienting the intraocular lens 80. Alternatively, the slip zones 90 can impart or diminish mechanical or structural properties associated with the optic portion 86. For example, some degree of accommodation can be provided to the optic portion 86 by the slip zones 90 as one portion of a slip zone displaces with respect to the other portion (e.g., a slide motion). The location of the slip zones 90, 92 may be pre-determined based on known properties of the intraocular lens 80, the refractive profile of the eye, and the like, displayed as defaults, altered and/or indicated by the operator, such via a user interface.

Figure 8:
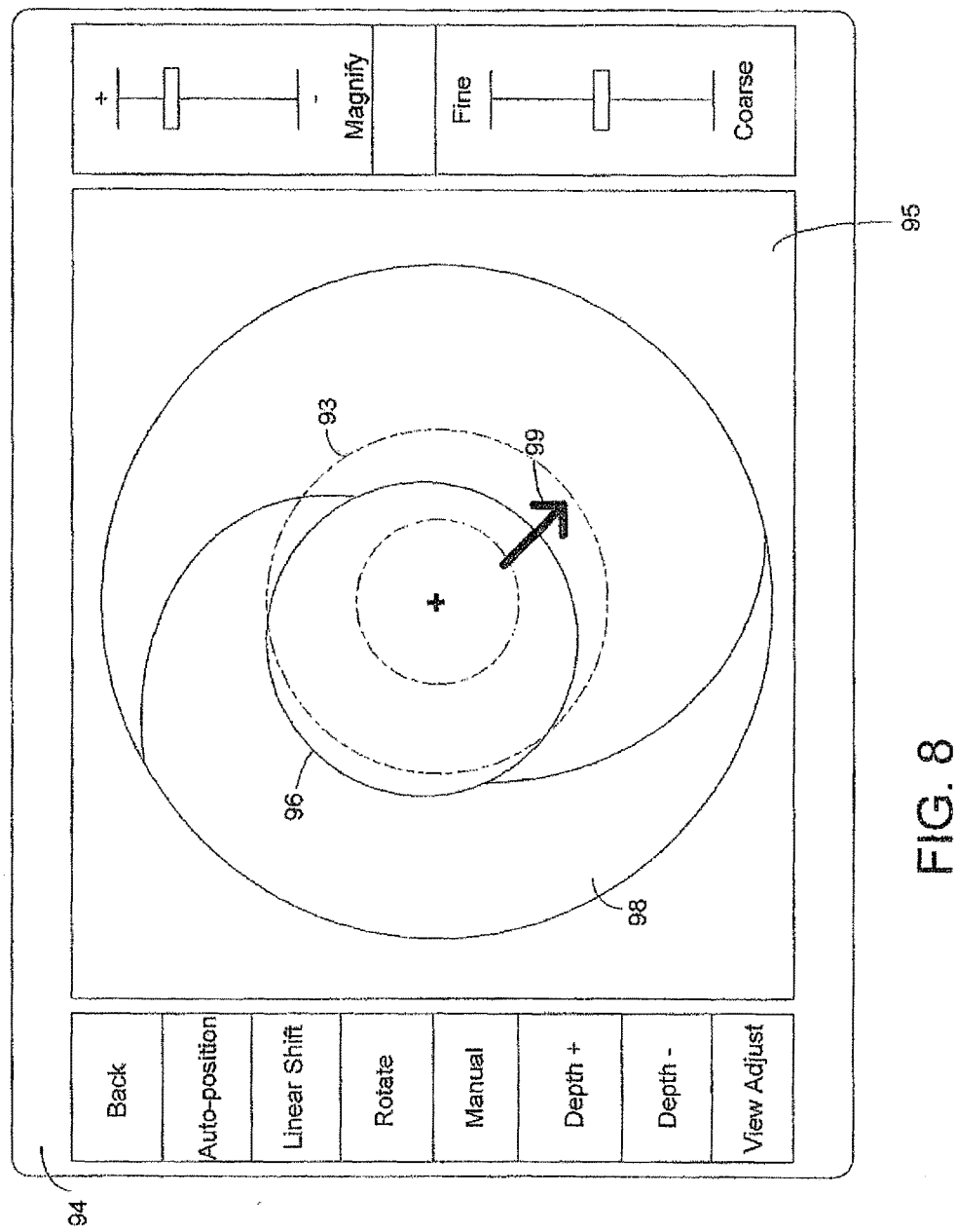
FIG. 8 is a front view of a display illustrating an intraocular lens modification in accordance with one embodiment.

FIG. 8 is a front view of a user interface 94 illustrating an intraocular lens re-orientation in accordance with one embodiment. The user interface 94 has a touch-sensitive screen 95 displaying a real-time image of an implanted intraocular lens 96 and provides a variety of system controls (e.g., selectable touch-sensitive buttons). Other representations of the implanted intraocular lens 96 may be displayed by the user interface 94 (e.g., based on real-time wavefront analysis, historical data of the patient's eye, and the like). The intraocular lens 96 is implanted in the capsular bag 98 of a patient's eye. In this embodiment, the operator has indicated a desired re-orientation of the intraocular lens 96 via a directional symbol 99 (e.g., an arrow). For example, the operator can use a stylus to draw the directional symbol 99 on the user interface 94. The placement of the directional symbol 99 as well as other characteristics of the directional symbol 99 (e.g., the length, shape, and the like) is detected by an image recognition application, and proposed modifications to the intraocular lens 96 can be determined and displayed by the user interface 94 to the operator.

The user interface 94 includes a "Back" button configured to return the displayed menu of system controls to a prior displayed menu, an "Auto-position" button configured to indicate a pre-determined re-orientation of the intraocular lens 96 on the displayed image (e.g., as an overlay image), a "Linear Shift" button configured to interpret the directional symbol 99 as a linear displacement, a "Rotate" button configured to interpret the directional symbol 99 as a rotational displacement, a "Manual" button configured to indicate a direct correlation of the directional symbol 99 with the desired displacement, a "Depth+" button configured to increase the focal plane depth of the displayed image, a "Depth−" button configured to decrease the focal plane depth of the displayed image, a "View Adjust" button configured to recall a menu of different views corresponding to the displayed image, a "Magnify" slide button configured to vary the displayed image magnification, and a "Fine/Coarse" slide button configured to vary the magnitude of displacement indicated by the directional symbol 99. A variety of other functions or combinations of some of the foregoing system controls may be provided by the user interface 94 via one or more of the same or different input mechanisms.

Additionally, the user interface displays a centration aid 93 as an overlay image, which may assist in determining the re-orientation of the intraocular lens 96 (e.g., with respect to a pre-determined reference). Following the selection or indication of the desired re-orientation, a suitable scan pattern is determined to direct the pulsed laser beam at the corresponding sub-surface regions of the intraocular lens 96.

Figure 9:
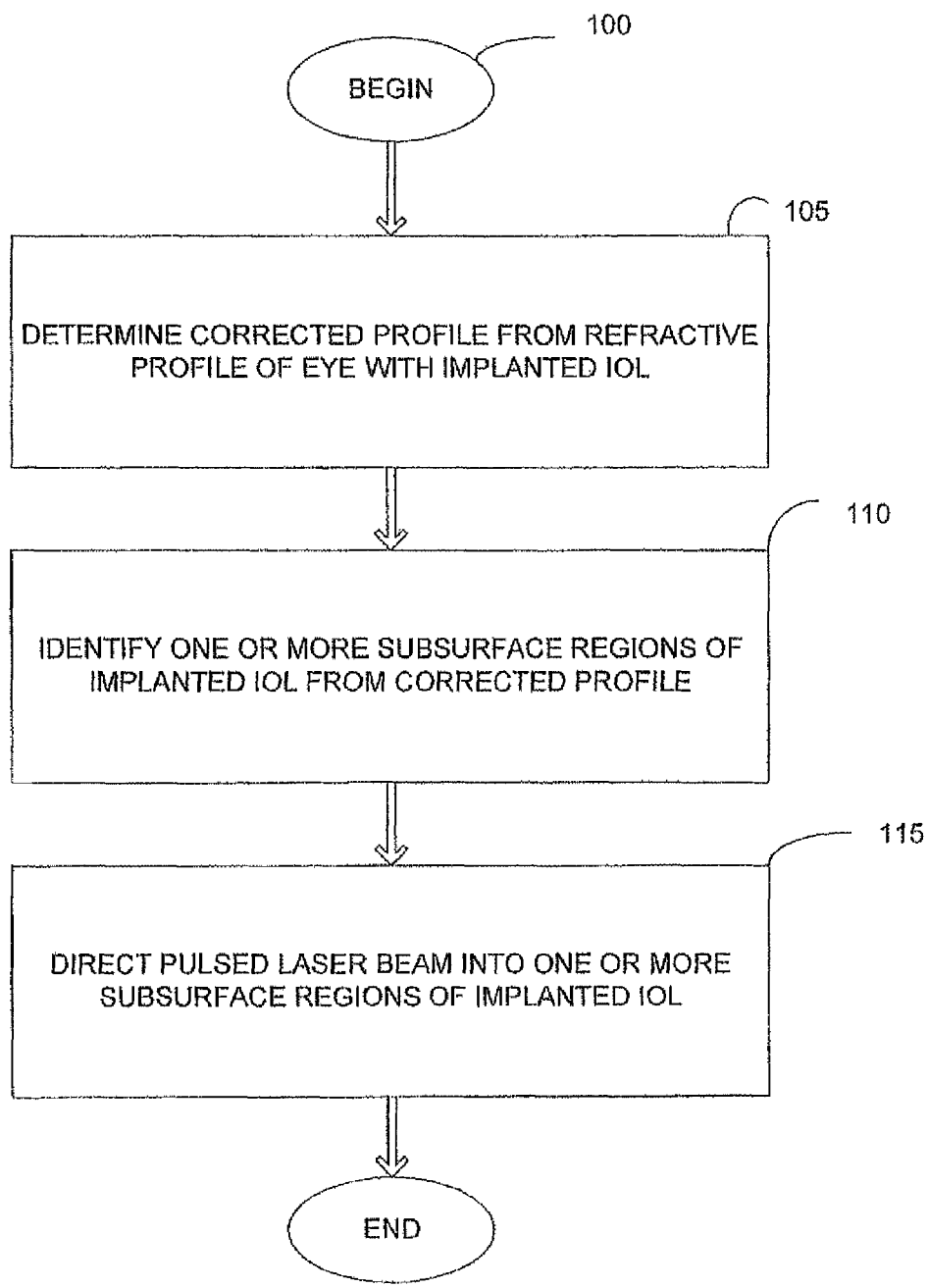
FIG. 9 is a flow diagram of a method for modifying a refractive profile of an eye having an intraocular lens implanted therein in accordance with one embodiment.

FIG. 9 is a flow diagram of a method 100 for modifying a refractive profile of an eye having an intraocular device implanted therein in accordance with one embodiment. A corrected refractive profile is determined based on an initial refractive profile of an eye, as indicated at 105. Referring to FIGS. 1 and 2, for example, the initial or starting refractive profile of the eye 12 can be determined using wavefront analysis techniques prior to modification of the intraocular lens 30. In one embodiment, the intraocular lens 30 is determined to be in an initial position within the eye 12. A corrected position of the intraocular lens 30 can be determined (e.g., by modeling in situ mechanical behavior of the intraocular lens 30 using known mechanical or structural characteristics of the intraocular lens 30, real-time or historical wavefront analysis of the eye 12 with the implanted intraocular lens 30, and the like) based on a re-orientation of the intraocular lens 30 to produce the corrected refractive profile.

One or more locations within the intraocular device are identified based on the corrected refractive profile, as indicated at 110. For example, the controller 22 determines which sub-surface regions of the intraocular lens 30 (e.g., within one or more haptics or support elements, within the optic, or within both) are to be irradiated with the pulsed laser beam 18 to produce the corresponding re-orientation of the intraocular lens 30 (resulting in the corrected refractive profile). The locations within the intraocular device may also be determined by the operator or through a combination of controller 22 and operator input.

A pulsed laser beam is directed at the one or more locations within the intraocular device to produce the corrected refractive profile, as indicated at 115. In one embodiment, the intraocular device is displaced from the initial position within the eye (e.g., pre-modification) to a corrected position within the eye based on directing the femtosecond laser beam at the one or more locations. Referring to FIGS. 4-6, examples are shown of displacing the intraocular lens 80 from the initial position (shown in broken line) to the corrected position. The corrected position of the intraocular device within the eye at least partially implements the corrected refractive profile.

The pulsed laser beam 18 may have a pre-determined pulse energy less than or equal to about 800 nanojoules/pulse, a pre-determined pulse width between about 300 picoseconds and about 10 femtoseconds, and/or a pre-determined wavelength between about 400 nm to about 3000 nm. Typically, the intraocular lens 30 is located within the capsular bag (e.g., following implantation/insertion and prior to modification). The intraocular device 30, or portions thereof, may have a pre-determined thermal threshold (e.g., a glass transition temperature) or a pre-determined viscoelasticity. In one example, the pulsed laser beam 18 is directed into the capsular bag and into the intraocular lens 30 at the sub-surface regions (e.g., by scanning) to heat these sub-surface regions above the thermal threshold. The mechanical or structural characteristic of the intraocular lens 30 is thus modified by such heating, and the intraocular lens 30 may then be re-oriented within the eye 12 (e.g., horizontally displaced, vertically displaced, displaced towards the cornea, displaced towards the retina, rotated, tilted, and the like, or any combination thereof). In another example, referring to FIG. 7, one or more slip zones 90, 92 may be formed at the sub-surface regions via the pulsed laser beam 18 to re-orient the intraocular lens 30 to the corrected position. The slip zones 90, 92 allow weakening, expansion, or rearrangement of the intraocular lens 30 to fit to the capsular bag, for example. This is particularly useful for enhancing or optimizing an accommodative effect of a suitably configured intraocular lens.

Figure 10:
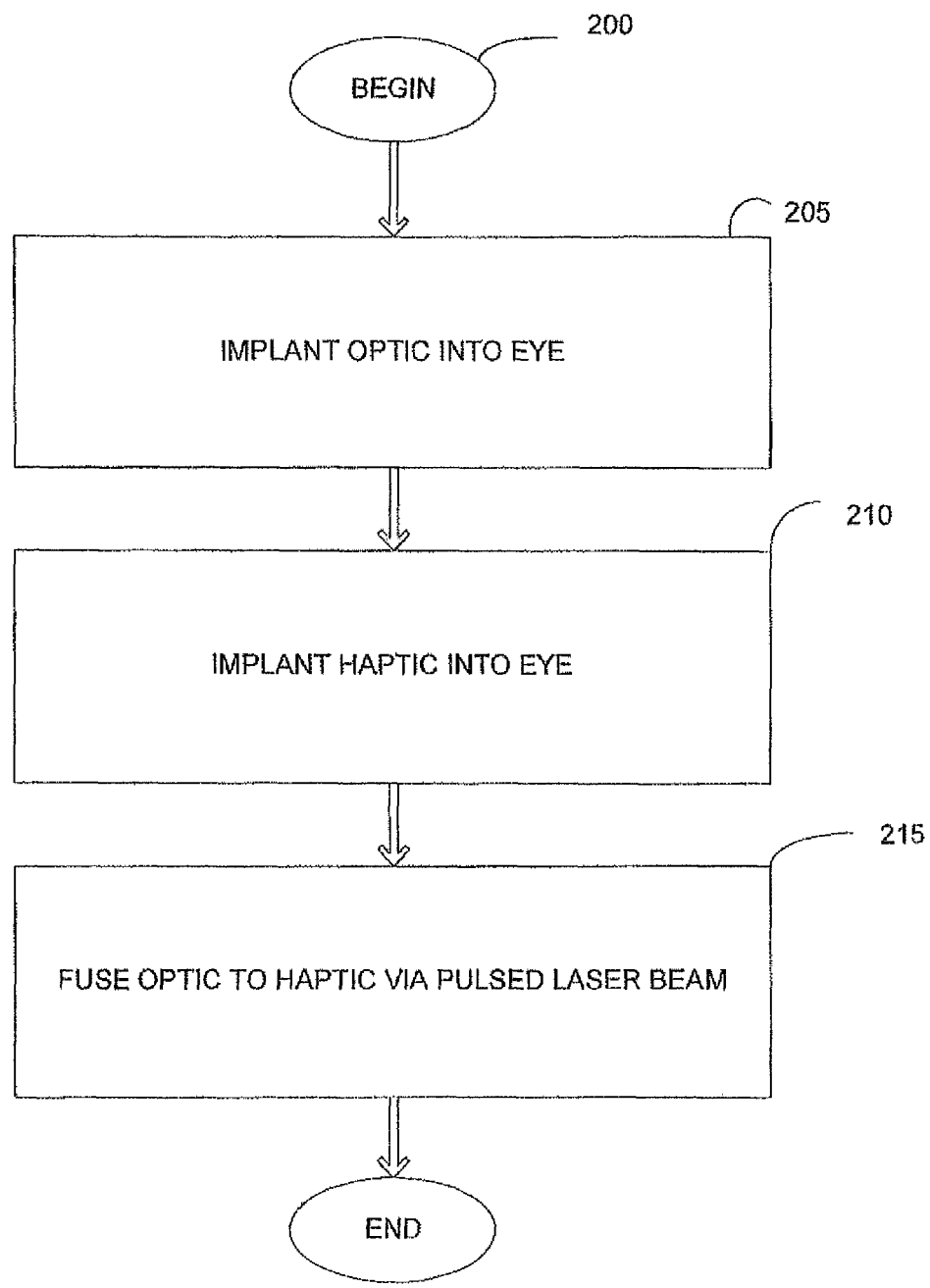
FIG. 10 is a flow diagram of a method modifying a refractive profile associated with an eye having an intraocular lens implanted therein in accordance with another embodiment.

In addition to modifying or re-orienting in situ intraocular lenses, FIG. 10 is a flow diagram of a method 200 for modifying a refractive profile associated with an eye in accordance with another embodiment. An optic is implanted within the eye, as indicated at 205. A support element (e.g., a haptic) is implanted within the eye, as indicated at 210. A pulsed laser beam is directed into the support element and the optic to fuse the support element to the optic, as indicated at 215. The resulting intraocular device within the eye (i.e., with the support element fused to the optic) modifies the refractive profile of the eye. In one embodiment, the support element may be partially coupled to the optic and implanted in this arrangement (e.g., to ease the insertion or implantation process). The intraocular lens may then be assembled in situ by fusing the support element to the optic. The pulsed laser beam may also fix the support element to the optic by other techniques, such as initializing polymerization and the like.

Thus, the systems 10, 40 can precisely modify and/or re-orient in situ intraocular lenses while minimizing particulate generation during this process. While embodiments of this invention have been shown and described, it will be apparent to those skilled in the art that many more modifications are possible without departing from the inventive concepts herein.

What is claimed is:

1. A method of modifying a refractive profile of an eye, the eye having an intraocular device implanted therein located at an initial position within the eye and the eye having an initial refractive profile, the method comprising the steps of:

determining a corrected refractive profile for the eye based on the initial refractive profile;

identifying one or more locations within the intraocular device based on the corrected refractive profile, the one or more locations within the intraocular device having a thermal threshold;

selecting properties of a femtosecond pulsed laser beam based on the thermal threshold, the properties including one or more of a pulse energy, a pulse width, a pulse repetition rate, a spot separation, an exposure time, and a scan pattern, the femtosecond laser having a pulse width between about 300 picoseconds and about 10 femtoseconds; and based on the selected properties, directing the femtosecond pulsed laser beam at the one or more locations to heat the one or more locations above the thermal threshold, wherein the intraocular device is re-oriented by the heating to a corrected position within the eye and produces the corrected refractive profile.

2. The method of claim 1, wherein the intraocular device is re-oriented in response to the directed pulsed laser beam by at least one of the group consisting of a horizontal displacement, a vertical displacement, a rotation, a tilt, a displacement towards a cornea of the eye, and a displacement toward a retina of the eye.

3. The method of claim 1, wherein the thermal threshold is a glass transition temperature of a material of the intraocular device at the one or more locations.

* * * * *